US012680922B2

(12) United States Patent
Warming et al.

(10) Patent No.: US 12,680,922 B2
(45) Date of Patent: Jul. 14, 2026

(54) SPATIAL-DEPENDENT ANALYSIS OF BIOLOGICAL MATERIAL FROM INTACT TISSUE SAMPLES

(71) Applicant: Genentech, Inc., South San Francisco, CA (US)

(72) Inventors: Soren Warming, South San Francisco, CA (US); Xin Ye, South San Francisco, CA (US); Jun Zou, South San Francisco, CA (US); Jonas Doerr, South San Francisco, CA (US); Michelle Dourado, South San Francisco, CA (US); Matthew Chang, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 934 days.

(21) Appl. No.: 17/932,895

(22) Filed: Sep. 16, 2022

(65) Prior Publication Data

US 2023/0123270 A1     Apr. 20, 2023

Related U.S. Application Data

(63) Continuation of application No. PCT/US2021/022804, filed on Mar. 17, 2021.

(60) Provisional application No. 63/074,693, filed on Sep. 4, 2020, provisional application No. 62/991,583, filed on Mar. 18, 2020.

(51) Int. Cl.
| | |
|---|---|
| *G01N 1/30* | (2006.01) |
| *C12Q 1/6869* | (2018.01) |
| *G01N 21/64* | (2006.01) |
| *G01N 33/58* | (2006.01) |

(52) U.S. Cl.
CPC .......... *G01N 1/30* (2013.01); *G01N 21/6402* (2013.01); *G01N 33/582* (2013.01); *C12Q 1/6869* (2013.01)

(58) Field of Classification Search
None
See application file for complete search history.

(56) References Cited

FOREIGN PATENT DOCUMENTS

| | | |
|---|---|---|
| CN | 1226147 A | 8/1999 |
| JP | 2004301681 A | 10/2004 |
| JP | 2019507352 A | 3/2019 |
| WO | 9818398 A1 | 5/1998 |
| WO | 2015097313 A1 | 7/2015 |

(Continued)

OTHER PUBLICATIONS

Rocco et al. Fluorescence-based cell-specific detection for laser-capture microdissection in human brain. Scientific Reports 7:14213 (2017) (Year: 2017).*

(Continued)

*Primary Examiner* — Samuel C Woolwine
(74) *Attorney, Agent, or Firm* — Baker Botts L.L.P.

(57) ABSTRACT

Biological research requires isolation and analysis of material, for example, RNA, DNA and protein, from tissue samples. The methods and compositions described herein allow for high resolution imaging of large and intact tissue samples, and subsequent isolation of material in a precise and location dependent-manner. The methods and compositions described herein may be used, for example, for biomarker discovery, identification of cell populations, pathology analysis, and generation of expression data in specific regions of interest.

15 Claims, 24 Drawing Sheets

(56) References Cited

FOREIGN PATENT DOCUMENTS

| WO | 2017031249 A1 | 2/2017 |
| WO | 2017188264 A1 | 11/2017 |
| WO | WO 2018/170515 A1 | 9/2018 |
| WO | WO 2018/224289 A1 | 12/2018 |
| WO | 2019009300 A1 | 1/2019 |
| WO | 2019015093 A1 | 1/2019 |
| WO | 2019147899 A1 | 8/2019 |
| WO | 2021188704 A1 | 9/2021 |

OTHER PUBLICATIONS

BASF Quadrol® Specialty Polyol [online] [retrieved on Feb. 20, 2026] retrieved from https://www.lookpolymers.com/pdf/BASF-Quadrol-Specialty-Polyol.pdf (Year: 2026).*

International Search Report and Written Opinion for Application No. PCT/US2021/022804, mailed on Jul. 8, 2021, 12 pages.

Lee et al. (Jan. 11, 2016) "ACT-PRESTO: Rapid and Consistent Tissue Clearing and Labeling Method for 3-dimensional (3d) Imaging", Scientific Reports, 6:18631 (15 pages).

Olson et al. (Aug. 1, 2016) "Multiphoton Microscopy With Clearing for Three Dimensional Histology of Kidney Biopsies", Biomedical Optics Express, 7(8):3089-3096.

Rodrigues et al. (Mar. 2019) "Slide-seq: A Scalable Technology for Measuring Genome-wide Expression at High Spatial Resolution", Science, 363(6434):1463-1467.

Schwarz et al. (May 20, 2015) "Fluorescent-Protein Stabilization and High-Resolution Imaging of Cleared, Intact Mouse Brains", PLos one, 10:1-26.

Wang et al. (Jul. 27, 2018) "Three-dimensional Intact-tissue Sequencing of Single-cell Transcriptional States", Science, 361(6400):5691 (22 pages).

* cited by examiner fixed mouse brain fixed cleared mouse brain

FIG. 3A

Adapted from: *J. Mater. Chem. B*, 2013, 1, 2750-2756

Photoactivation
of spinal
cord tissue

FIG. 9A

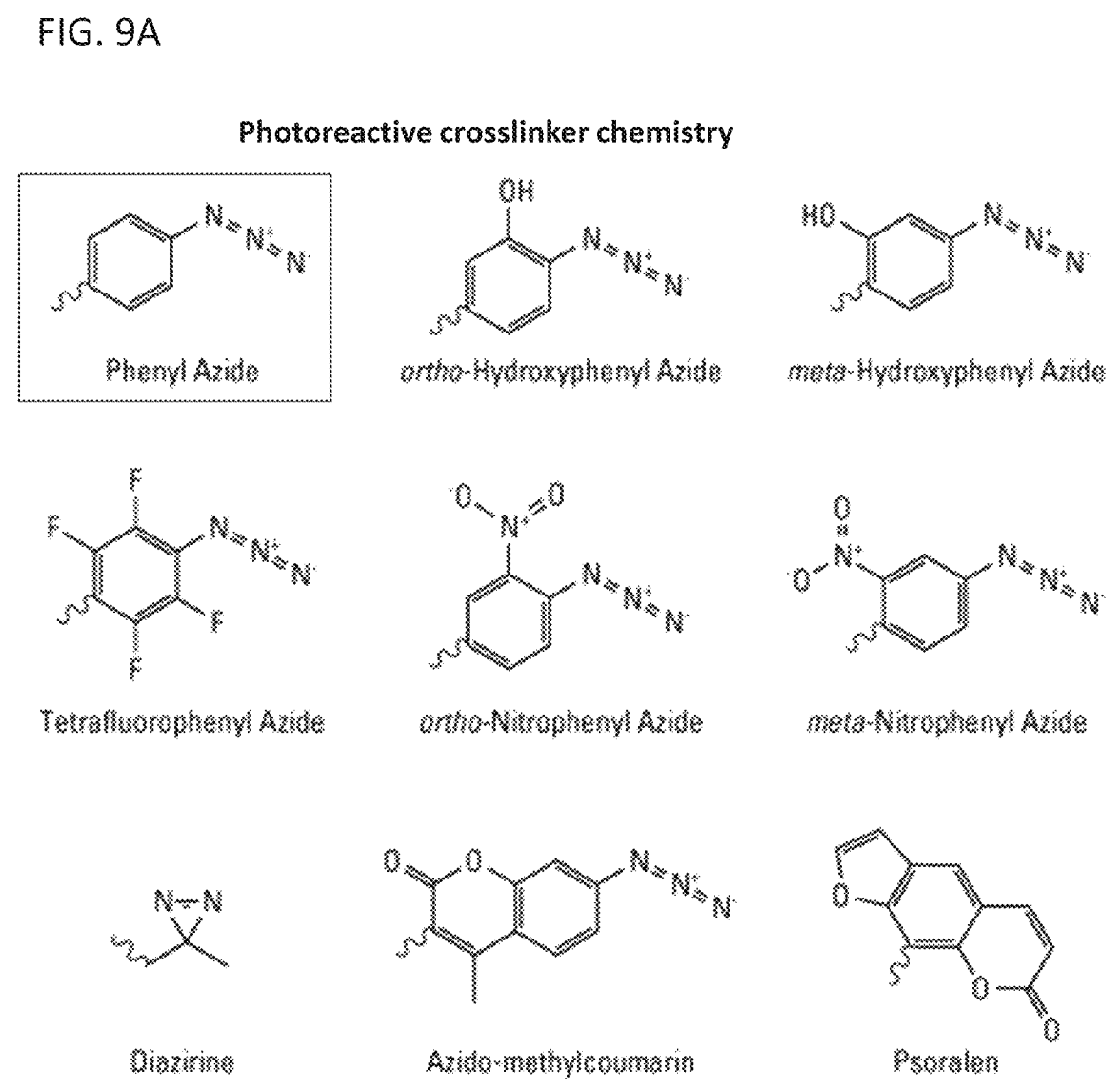

Photoreactive crosslinker chemistry

Phenyl Azide

*ortho*-Hydroxyphenyl Azide

*meta*-Hydroxyphenyl Azide

Tetrafluorophenyl Azide

*ortho*-Nitrophenyl Azide

*meta*-Nitrophenyl Azide

Diazirine

Azido-methylcoumarin

Psoralen

FIG. 9C

Alexa488 meta-Nitrophenyl Azide

Cy3 meta-Nitrophenyl Azide

FIG. 9C (continued)

Cy5 meta-Nitrophenyl Azide

Biotin meta-Nitrophenyl Azide

Expression profiling of cell types

UMAP

Number of genes per cell

SPATIAL-DEPENDENT ANALYSIS OF BIOLOGICAL MATERIAL FROM INTACT TISSUE SAMPLES

CROSS-REFERENCE TO RELATED APPLICATIONS

This application is a Continuation of International Application No. PCT/US2021/022804, filed Mar. 17, 2021, which claims priority to U.S. Provisional Application No. 62/991,583, filed on Mar. 18, 2020, and U.S. Provisional Application No. 63/074,693, filed on Sep. 4, 2020, each of which is incorporated herein by reference in its entirety for all purposes.

BACKGROUND

During the majority of molecular biology-based methods for tissue analysis, the spatial context of the analyzed material is lost. Techniques known in the art that do combine sequence analysis with spatial information have limitations, for instance, low sequencing depth, sample volume restrictions, analysis of individual tissue sections, or time-consuming read-out, among other constraints. Currently, to the best of our knowledge, there are no methods available that combines the precision of isolation with depth of analysis. The methods and compositions described herein address these and other problems in the art.

SUMMARY

The instant technology generally relates to methods and compositions for three-dimensional labelling of cells or other region of a tissue or tissue sample. The methods include imaging of a cleared tissue or sample that has been labeled by contacting a region (or cell) of interest with an appropriate label, and then subjecting said region (or cell) of interest to a multi-photon laser. The labeled region can then be isolated from the tissue or sample and subjected to analysis, such as, and not limited to, DNA sequencing, RNA sequencing, proteomic analysis, epigenetic analysis, immunohistochemistry analysis, chromosome conformation capture, or immunofluorescence analysis. Various methods of isolation of the labeled region (or cell) of interest can be used, such as, and not limited to, laser-assisted microdissection, fluorescence-assisted cell sorting (FACS), magnetic-activated cell sorting (MACS), or buoyancy activated cell sorting (BACS). Such analysis can provide information about discrete regions of the tissue or sample.

In an aspect is provided a method for labeling a region of a tissue or tissue sample. The method may include: a) providing a three-dimensional tissue or tissue sample; b) clearing the sample; c) contacting the tissue or tissue sample with a photo-activatable label; and d) subjecting a region of the tissue or tissue sample to a multi-photon laser, thereby labeling the region.

In another aspect is provided a method for 3-dimensional expression profiling of an intact tissue or tissue sample. The method may include: a) providing a three-dimensional intact tissue or tissue sample; b) clearing the sample; c) contacting the tissue or tissue sample with photo-activatable label; d) subjecting a region of the tissue or tissue sample to a multi-photon laser, thereby labeling the region; e) imaging the labeled region to create an image; f) isolating the labeled region from the tissue or tissue sample; g) determining a DNA, RNA, and/or protein composition of the isolated labeled region; h) combining the image with the DNA, RNA, and/or protein composition of the isolated labeled region to create a 3-dimensional expression profile of the intact tissue or tissue sample.

In an aspect, a method for isolating a single cell or a nucleus, in a tissue or tissue sample is provided. The method may include: a) providing a three-dimensional tissue or tissue sample comprising a cell or nucleus of interest; b) clearing the sample; c) contacting the tissue or tissue sample with photo-activatable label; d) subjecting the cell or nucleus to a multi-photon laser, thereby labeling the cell or nucleus; e) dissociating the labeled cell nucleus from the tissue or tissue sample; and (f) isolating the labeled cell or nucleus.

In another aspect, a composition is provided. The composition may include a tissue sample, a medium having a refraction index similar to or matching the tissue, and a photo-activatable label.

In an aspect, a cleared tissue sample is provided. The cleared tissue sample may include a photo-activatable label and a medium having a refraction index substantially matching the index of the tissue.

BRIEF DESCRIPTION OF THE DRAWINGS

Figure 3A:
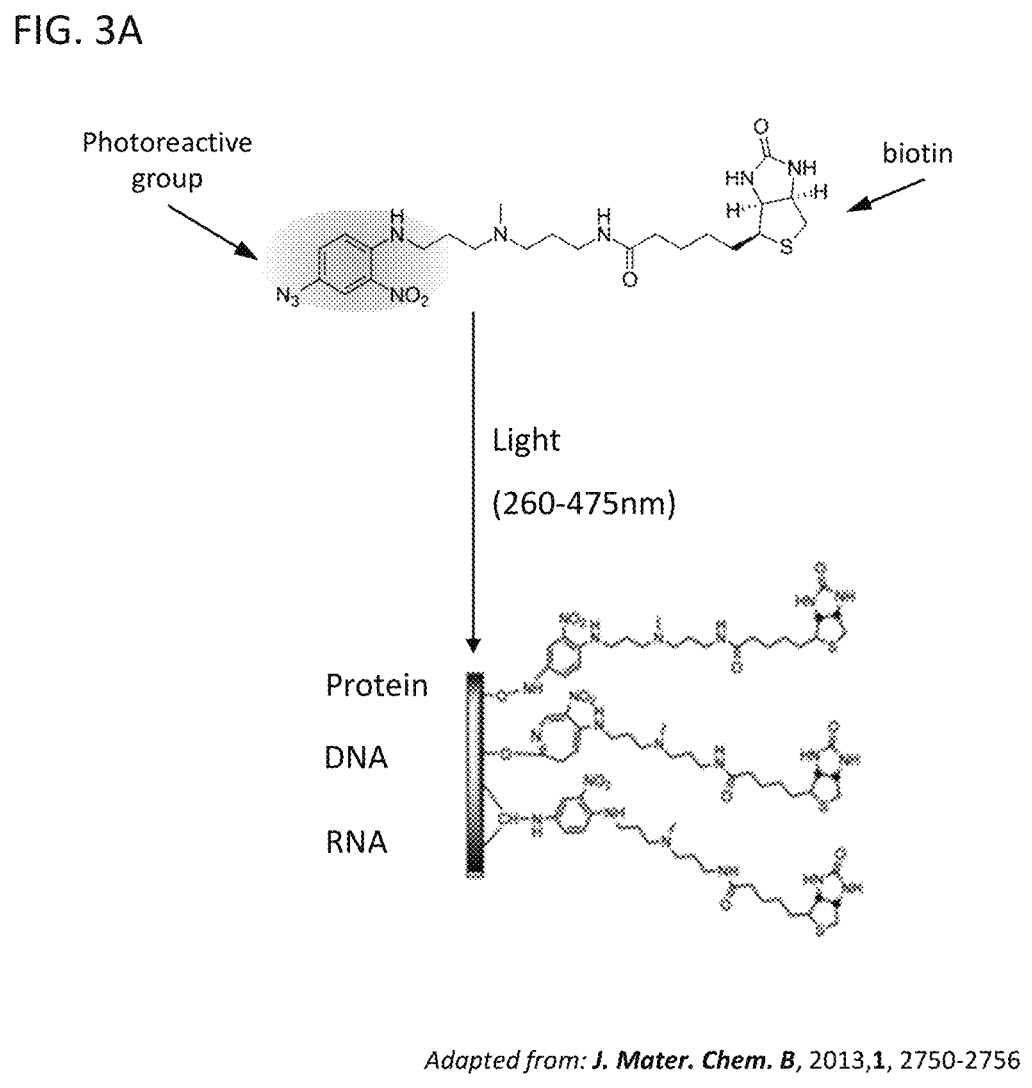

FIGS. 3A-B are drawings showing an embodiment of the use of 2-photon microscopy to label a cell or nucleus of interest in a cleared tissue, using a photoreactive label. FIG. 3A is a drawing showing the labeling of molecules with a photoreactive label with a photoreactive group and a biotin tag, when the label is exposed to light of wavelength between 260 nm and 475 nm. FIG. 3B is a drawing presenting the advantages of the use of 2-photon microscopy (right) to label a cell or a nucleus of interest in comparison to conventional confocal microscopy (left). Traditional confocal microscopy results in photoactivation of the entire area of the tissue that is exposed to both the light (red) and the photo-activatable compound (green). In contrast, 2-photon microscopy allows more accurate photoactivation and a target site (red star), thus avoiding non-specific labeling of non-targeted tissue.

FIG. 6A shows an example tissue clearing (FIG. 6A, panel A) and labeling process (panels B-E), and isolation of photolabeled nuclei (panel F). The resulting samples can be analyzed by SPLiT seq library preparation from the isolated photolabeled nuclei (panels G and H), with subsequent data analysis (I). In addition (or alternatively), DNA (FIG. 6B) or protein (FIG. 6C) from the isolated tissue may be analyzed.

FIG. 7A is a plot showing unique count per barcode (log2(UMI)) as function of barcode rank (barcode log10 scale). FIG. 7B is a scatter plot showing log2(TPM) for fixed samples on the y-axis and log2(TPM) for cleared samples on the x-axis (TPM: Transcripts per million). FIG. 7C shows an example genome browser window presenting the cDNA coverage of a 72 kb stretch of Mouse (mm10) chromosome 2 (top), with a comparison of fixed and cleared (center) and fixed (bottom) samples. For FIGS. 7A-7C, spinal cord was photoactivated in Cy3-PA. Nuclei were extracted and sorted for label incorporation. A SPLiT-seq library was generated and sequenced by HiSeq.

FIG. 8A is a drawing of a cross section of a mouse spinal cord illustrates different areas of the spinal cord with dorsal layers indicated as colored circles. In the magnified panel, an area is highlighted that was subjected to photoactivation. FIG. 8B is a FACS plot of cleared, but not photoactivated nuclei isolated from a mouse spinal cord. The Y axis shows the signal for DAPI, a nuclear counterstain, while the X axis shows the PA dye used for this experiment: Cy3-PA. The boxes indicate single nuclei negative for incorporated Cy3 (left) or positive for incorporated Cy3 (right). FIG. 8C is a FACS plot of cleared, and photoactivated nuclei isolated from a mouse spinal cord (indicated in FIG. 9A). The Y axis shows the signal for DAPI, a nuclear counterstain, while the X axis shows the PA dye used for this experiment: Cy3-PA. The boxes indicate single nuclei negative for incorporated Cy3 (left) or positive for incorporated Cy3 (right).

FIGS. 9A-9C present example compounds for use in the methods of the present invention. FIG. 9A shows examples of photoreactive compounds that could be used for photo-labeling. FIG. 9B shows example modifications to aryl azides induced by ultraviolet (UV) light. FIG. 9C shows examples of synthesized photoreactive compounds.

FIG. 10A is a graph showing the expression profiling of cell types (expression level of genes associated with the indicated cell type). FIG. 10B is a graph generated by UMAP of the data in FIG. 10A.

DETAILED DESCRIPTION

Figure 1:
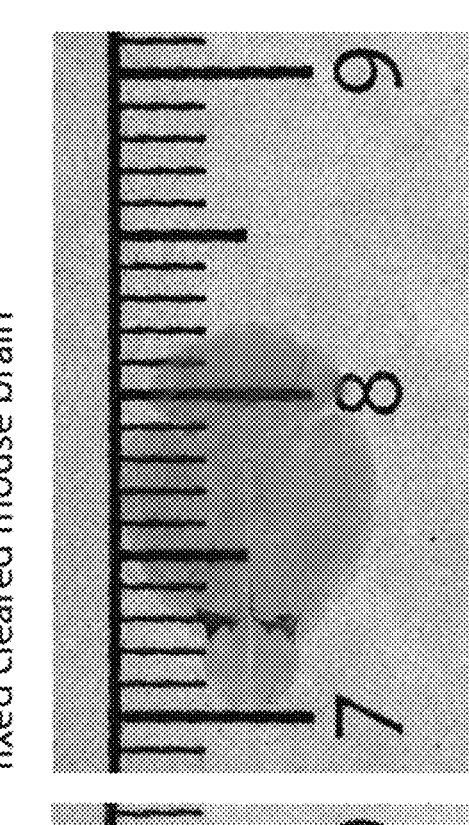
FIG. 1 shows a mouse brain before (left) and after (right) clearing of the tissue.

After reading this description it will become apparent to one skilled in the art how to implement the present disclosure in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present disclosure as set forth herein.

Before the present technology is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description divided into various sections only for the reader's convenience and disclosure found in any section may be combined with that in another section. Titles or subtitles may be used in the specification for the convenience of a reader, which are not intended to influence the scope of the present disclosure.

Definitions

Unless defined otherwise, all technical and scientific terms used herein have the same meaning as commonly understood by one of ordinary skill in the art to which this disclosure belongs. In this specification and in the claims that follow, reference will be made to a number of terms that shall be defined to have the following meanings:

The terminology used herein is for the purpose of describing particular embodiments only and is not intended to be limiting. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to a dose amount means that the dose may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this disclosure.

Methods

In an aspect is provided a method for labeling a region of a tissue or tissue sample. The method may include (a) providing a three-dimensional tissue or tissue sample; (b) clearing the sample; (c) contacting the tissue or tissue sample with a photo-activatable label; and (d) subjecting a region of the tissue or tissue sample to a multi-photon laser, thereby labeling the region. In embodiments, the multi-photon laser is a two-photon laser. In embodiments, the multi-photon laser is a three-photon laser.

For the methods provided herein, in embodiments, the region includes a cell, a subcellular compartment, an aggregate, or a secreted aggregate. In embodiments, the region includes a cell. In embodiments, the region includes a subcellular compartment. In embodiments, the region includes an aggregate. In embodiments, the region includes a secreted aggregate. In embodiments, the subcellular compartment is a nucleus.

In embodiments, the method further includes imaging the tissue or tissue sample. In embodiments, the method further includes imaging the tissue. In embodiments, the method further includes imaging the tissue sample. In embodiments, the tissue or tissue sample is a fixed tissue or fixed tissue sample. In embodiments, the tissue is a fixed tissue. In embodiments, the tissue is a fixed tissue sample. In embodiments, the tissue sample is a fixed tissue. In embodiments, the tissue sample is a fixed tissue sample.

For the methods provided herein, in embodiments, the photo-activatable label includes a detectable moiety. In embodiments, the detectable moiety includes a light emitting moiety. In embodiments, the light emitting moiety is a fluorescent moiety, a chemiluminescent moiety, a bioluminescent moiety, or an electrochemiluminescent moiety. In embodiments, the light emitting moiety is a fluorescent moiety. In embodiments, the light emitting moiety is a chemiluminescent moiety. In embodiments, the light emitting moiety is a bioluminescent moiety. In embodiments, the light emitting moiety is an electrochemiluminescent moiety. In embodiments, the fluorescent moiety includes a fluorophore. In embodiments, one of the detectable moiety includes an antibody or a functional derivative thereof. In embodiments, photo-activatable label includes a tag. In embodiments, the tag is chosen from the group including an affinity tag, an epitope tag, a fluorescent tag, an oligonucleotide tag, or a biotin tag. In embodiments, the tag is an affinity tag. In embodiments, the tag is an epitope tag. In embodiments, the tag is a fluorescent tag. In embodiments, the tag is an oligonucleotide tag. In embodiments, the tag is a biotin tag.

For the methods provided herein, in embodiments the sample clearing process includes dehydrating the sample and transferring the sample into a medium with a refraction index similar to or matching the tissue. In embodiments, the refractive index is between about 1.3 and about 1.6. In embodiments, the refractive index is about 1.3. In embodiments, the refractive index is about 1.325. In embodiments, the refractive index is about 1.35. In embodiments, the refractive index is about 1.375. In embodiments, the refractive index is about 1.4. In embodiments, the refractive index is about 1.425. In embodiments, the refractive index is about 1.45. In embodiments, the refractive index is about 1.475. In embodiments, the refractive index is about 1.5. In embodiments, the refractive index is about 1.525. In embodiments, the refractive index is about 1.55. In embodiments, the refractive index is about 1.575. In embodiments, the refractive index is about 1.6. In embodiments, the refractive index is about 1.3, about 1.325, about 1.35, about 1.375, about 1.4, about 1.425, about 1.45, about 1.475, about 1.5, about 1.525, about 1.55, about 1.575, or about 1.6. The reflective index may be any value or subrange within the recited ranges, including endpoints, or any range between any of the recited values.

In embodiments, the medium includes a solution of Benzyl Alcohol, Benzyl Benzoate (BABB) or derivative thereof, with or without one or more of triethylamine, diphenyl ether, dibenzyl ether, α-tocopherol, and/or Quadrol. In embodiments, the medium includes a solution of Benzyl Alcohol with one or more of triethylamine, diphenyl ether, dibenzyl ether, α-tocopherol, and/or Quadrol. In embodiments, the medium includes a solution of Benzyl Alcohol without one or more of triethylamine, diphenyl ether, dibenzyl ether, α-tocopherol, and/or Quadrol. In embodiments, the medium includes a solution of Benzyl Benzoate (BABB) or derivatives thereof, with one or more of triethylamine, diphenyl ether, dibenzyl ether, α-tocopherol, and/or Quadrol. In embodiments, the medium includes a solution of Benzyl Benzoate (BABB) or derivatives thereof, without one or more of triethylamine, diphenyl ether, dibenzyl ether, α-tocopherol, and/or Quadrol. In embodiments, the medium includes a BABB solution.

As mentioned above for the methods provided herein, in embodiments the sample clearing process includes dehydrating the sample. In embodiments, the sample is dehydrated by a tert-butanol solution. In embodiments, the tert-butanol solution includes trimethylamine, tetrahydrofuran, ethanol, or methanol. In embodiments, the tert-butanol solution includes trimethylamine. In embodiments, the tert-butanol solution includes tetrahydrofuran. In embodiments, the tert-butanol solution includes ethanol. In embodiments, the tert-butanol solution includes methanol.

For the methods provided herein, in embodiments the photo-activatable label is hydrophobic. For the methods provided herein, in embodiments the photo-activatable label includes a phenyl azide group, an ortho-hydroxyphenyl azide group, a meta-hydroxyphenyl azide group, a tertrafluorophenyl azide group, an ortho-nitrophenyl azide group, a meta-nitrophenyl azide group, a diazirine group, an azido-methylcoumarin group, or a psoralen group. In embodiments the photo-activatable label includes a phenyl azide group. In embodiments the photo-activatable label includes an ortho-hydroxyphenyl azide group. In embodiments the photo-activatable label includes a meta-hydroxyphenyl azide group. In embodiments the photo-activatable label includes a tertrafluorophenyl azide group. In embodiments the photo-activatable label includes an ortho-nitrophenyl azide group. In embodiments the photo-activatable label includes a meta-nitrophenyl azide group. In embodiments the photo-activatable label includes a diazirine group. In embodiments the photo-activatable label includes an azido-methylcoumarin group. In embodiments the photo-activatable label includes a psoralen group. In embodiments, the photo-activatable label includes an aryl azide group.

In embodiments, the method further includes isolating the labeled region or a portion of the labeled region from the tissue or tissue sample. In embodiments, the method further includes isolating the labeled region from the tissue. In embodiments, the method further includes isolating a portion of the labeled region from the tissue. In embodiments, the method further includes isolating the labeled region from the tissue sample. In embodiments, the method further includes isolating a portion of the labeled region from the tissue sample. In embodiments, the labeled region or portion is isolated by FACS sorting for the label. In embodiments, the method further includes analyzing a composition of the isolated labeled region to create analysis data. In embodiments, analyzing includes determining a DNA, RNA, and/or protein composition of the isolated labeled region. In embodiments, analyzing includes determining a DNA, RNA, and protein composition of the isolated labeled region. In embodiments, analyzing includes determining a DNA, RNA, or protein composition of the isolated labeled region. In embodiments, analyzing includes determining a DNA composition of the isolated labeled region. In embodiments, analyzing includes determining a RNA composition of the isolated labeled region. In embodiments, analyzing includes determining a protein composition of the isolated labeled region. In embodiments, the RNA is analyzed by SPLITseq.

For the methods provided herein, in embodiments, the tissue or tissue sample was imaged to create an image prior to isolating the labeled region, further including combining the image with the analysis data to create a 3-dimensional composition map of the region.

In an aspect is provided a method for 3-dimensional expression profiling of an intact tissue or tissue sample. The method may include (a) providing a three-dimensional intact tissue or tissue sample; (b) clearing the sample; (c) contacting the tissue or tissue sample with photo-activatable label; (d) subjecting a region of the tissue or tissue sample to a multi-photon laser, thereby labeling the region; (e) imaging the labeled region to create an image; (f) isolating the labeled region from the tissue or tissue sample; (g) determining a DNA, RNA, and/or protein composition of the isolated labeled region; (h) combining the image with the DNA, RNA, and/or protein composition of the isolated labeled region to create a 3-dimensional expression profile of the intact tissue or tissue sample. In embodiments, the multi-photon laser is a two-photon laser. In embodiments, the multi-photon laser is a three-photon laser. In embodiments, the region is a cell, a subcellular compartment, an aggregate, or a secreted aggregate. In embodiments, the region is a cell. In embodiments, the region is a subcellular compartment. In embodiments, the region is an aggregate. In embodiments, the region is a secreted aggregate. In embodiments, the isolated labeled region is a single nuclei. In embodiments, an RNA composition of the isolated labeled region is determined.

In an aspect, a method for isolating a single cell or a nucleus, in a tissue or tissue sample is provided. The method may include (a) providing a three-dimensional tissue or tissue sample; (b) clearing the sample; (c) contacting the tissue or tissue sample with photo-activatable label; (d) subjecting a cell to a multi-photon laser, thereby labeling the cell; (e) dissociating the labeled cell from the tissue or tissue sample; and (f) isolating the labeled cell or nucleus. In embodiments, the multi-photon laser is a two-photon laser. In embodiments, the multi-photon laser is a three-photon laser.

In embodiments, the method further includes imaging the tissue or tissue sample. In embodiments, the method further includes imaging the tissue. In embodiments, the method further includes imaging the tissue sample. In embodiments, the tissue or tissue sample is a fixed tissue or fixed tissue sample. In embodiments, the tissue is a fixed tissue. In embodiments, the tissue is a fixed tissue sample. In embodiments, the tissue sample is a fixed tissue. In embodiments, the tissue sample is a fixed tissue sample.

For the methods provided herein, in embodiments, the photo-activatable label includes a detectable moiety. In embodiments, the detectable moiety includes a light emitting moiety. In embodiments, the light emitting moiety is a fluorescent moiety, a chemiluminescent moiety, a bioluminescent moiety, or an electrochemiluminescent moiety. In embodiments, the light emitting moiety is a fluorescent moiety. In embodiments, the light emitting moiety is a chemiluminescent moiety. In embodiments, the light emitting moiety is a bioluminescent moiety. In embodiments, the light emitting moiety is an electrochemiluminescent moiety. In embodiments, the fluorescent moiety includes a fluorophore. In embodiments, the detectable moiety includes an antibody or a functional derivative thereof. In embodiments, the photo-activatable label includes a tag. In embodiments, the tag is chosen from the group including an affinity tag, an epitope tag, a fluorescent tag, an oligonucleotide tag, or a biotin tag. In embodiments, the tag is an affinity tag. In embodiments, the tag is an epitope tag. In embodiments, the tag is a fluorescent tag. In embodiments, the tag is an oligonucleotide tag. In embodiments, the tag is a biotin tag.

For the methods provided herein, in embodiments, the sample clearing process includes dehydrating the sample and transferring the sample into medium with a refraction index similar to or matching the tissue. In embodiments, the medium includes a solution of Benzyl Alcohol, Benzyl Benzoate (BABB) or derivatives thereof, with or without one or more of triethylamine, diphenyl ether, dibenzyl ether, α-tocopherol, and/or Quadrol. In embodiments, the medium includes a solution of Benzyl Alcohol with one or more of triethylamine, diphenyl ether, dibenzyl ether, α-tocopherol, and/or Quadrol. In embodiments, the medium includes a solution of Benzyl Alcohol without one or more of triethylamine, diphenyl ether, dibenzyl ether, α-tocopherol, and/or Quadrol. In embodiments, the medium includes a solution of Benzyl Benzoate (BABB) or derivatives thereof, with one or more of triethylamine, diphenyl ether, dibenzyl ether, α-tocopherol, and/or Quadrol. In embodiments, the medium includes a solution of Benzyl Benzoate (BABB) or derivatives thereof, without one or more of triethylamine, diphenyl ether, dibenzyl ether, α-tocopherol, and/or Quadrol. In embodiments, the medium includes a BABB solution.

For the methods provided herein, in embodiments, the sample is dehydrated by a tert-butanol solution. In embodiments, the tert-butanol solution includes trimethylamine, tetrahydrofuran, ethanol, or methanol. In embodiments, the tert-butanol solution includes trimethylamine. In embodiments, the tert-butanol solution includes tetrahydrofuran. In embodiments, the tert-butanol solution includes ethanol. In embodiments, the tert-butanol solution includes methanol. In embodiments, the photo-activatable label is hydrophobic.

For the methods provided herein, in embodiments, the photo-activatable label includes a phenyl azide group, an ortho-hydroxyphenyl azide group, a meta-hydroxyphenyl azide group, a tertrafluorophenyl azide group, an ortho-nitrophenyl azide group, a meta-nitrophenyl azide group, a diazirine group, an azido-methylcoumarin group, or a psoralen group. In embodiments, the photo-activatable label includes a phenyl azide group. In embodiments, the photo-activatable label includes an ortho-hydroxyphenyl azide group. In embodiments, the photo-activatable label includes a meta-hydroxyphenyl azide group. In embodiments, the photo-activatable label includes a tertrafluorophenyl azide group. In embodiments, the photo-activatable label includes an ortho-nitrophenyl azide group. In embodiments, the photo-activatable label includes a meta-nitrophenyl azide group. In embodiments, the photo-activatable label includes a diazirine group. In embodiments, the photo-activatable label includes an azido-methylcoumarin group. In embodiments, the photo-activatable label includes a psoralen group. In embodiments, the photo-activatable label includes an aryl azide group. In embodiments, the photo-activatable label includes a group shown in FIG. 9A.

In embodiments, the methods provided herein further include isolating the labeled cell or nucleus. In embodiments, the methods further include isolating the labeled cell. In embodiments, the methods further include isolating the labeled nucleus. In embodiments, the labeled cell or nucleus is isolated by fluorescence activated cell sorting (FACS) sorting for the label. In embodiments, the labeled cell is isolated by FACS sorting for the label. In embodiments, the nucleus is isolated by FACS sorting for the label. In embodiments, the labeled cell or nucleus is isolated by magnetic-activated cell sorting (MACS) sorting for the label. In embodiments, the labeled cell is isolated by MACS sorting for the label. In embodiments, the labeled nucleus is isolated by MACS sorting for the label. In embodiments, the labeled cell or nucleus is isolated by buoyancy-activated cell sorting (BACS) sorting for the label. In embodiments, the labeled cell is isolated by BACS sorting for the label. In embodiments, the labeled nucleus is isolated by BACS sorting for the label. In embodiments, the labeled cell or nucleus is isolated by affinity-based column purification (e.g., affinity chromatography) sorting for the label. In embodiments, the labeled cell is isolated by affinity-based column purification sorting for the label. In embodiments, the labeled nucleus is isolated by affinity-based column purification sorting for the label In embodiments, the methods provided herein further include analyzing the isolated labeled cell or nucleus. In embodiments, the methods further include analyzing the isolated labeled cell. In embodiments, the methods further include analyzing the isolated labeled nucleus. In embodiments, the analyzing includes determining a DNA, RNA, and/or protein composition of the isolated labeled cell or nucleus. In embodiments, the analyzing includes determining a DNA, RNA, and protein composition of the isolated labeled cell or nucleus. In embodiments, the analyzing includes determining a DNA, RNA, or protein composition of the isolated labeled cell or nucleus. In embodiments, the analyzing includes determining a DNA composition of the isolated labeled cell or nucleus. In embodiments, the analyzing includes determining a RNA composition of the isolated labeled cell or nucleus. In embodiments, the analyzing includes determining a protein composition of the isolated labeled cell or nucleus. In embodiments, the analyzing includes determining a DNA composition of the isolated labeled cell. In embodiments, the analyzing includes determining a RNA composition of the isolated labeled cell. In embodiments, the analyzing includes determining a protein composition of the isolated labeled cell. In embodiments, the analyzing includes determining a DNA composition of the isolated labeled nucleus. In embodiments, the analyzing includes determining a RNA composition of the isolated labeled nucleus. In embodiments, the analyzing includes determining a protein composition of the isolated labeled nucleus. In embodiments, the RNA is analyzed by single-cell RNA sequencing (scRNAseq). In embodiments, the RNA is analyzed by SPLITseq.

Figure 11:
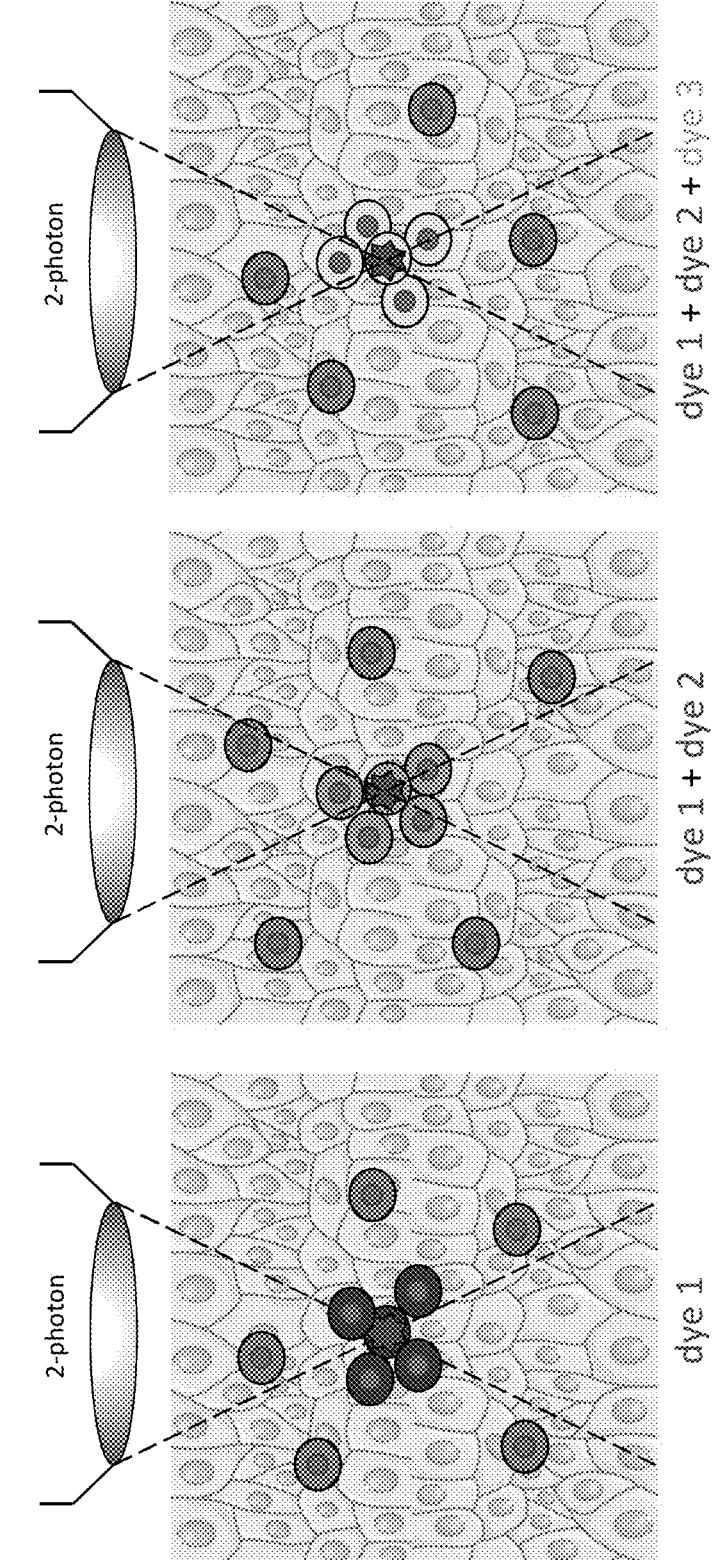
FIG. 11 is a cartoon of an example of how multiplexing can allow for multiple labeling events. A tissue can be exposed to a first dye (dye 1), followed by 2-photon labeling of a first area of interest (left panel). The same tissue can then be contacted with a second dye (dye 2) (optionally after washing), followed by 2-photon labeling of a second area of interest (middle panel). If desired, the same tissue can then be contacted with a third dye (dye 3) (optionally after washing), followed by 2-photon labeling of a third area of interest (right panel).
Figure 12A:
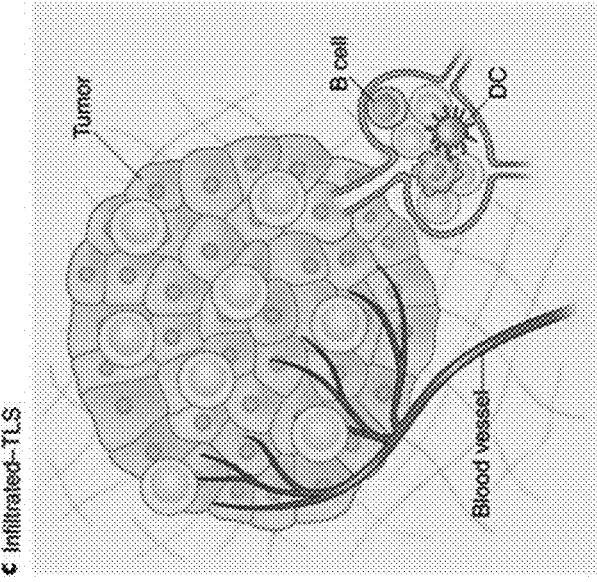
FIGS. 12A-12C present examples of application areas for targeted compounds for photoactivation in whole mounts. Application area examples include tumor heterogeneity, inflamed tumors/immune dessert and proximity to vascular system (FIG. 12A), finding and labeling sparse cell populations (FIG. 12B), generating expression data, and 3D histology (FIG. 12C).
Figure 12A:
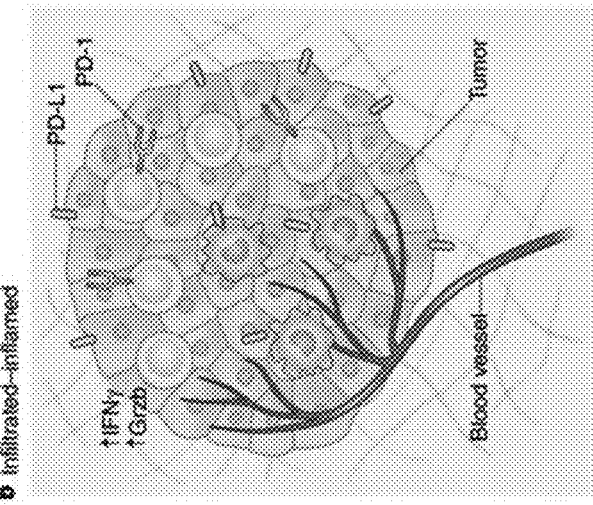
Figure 12A:
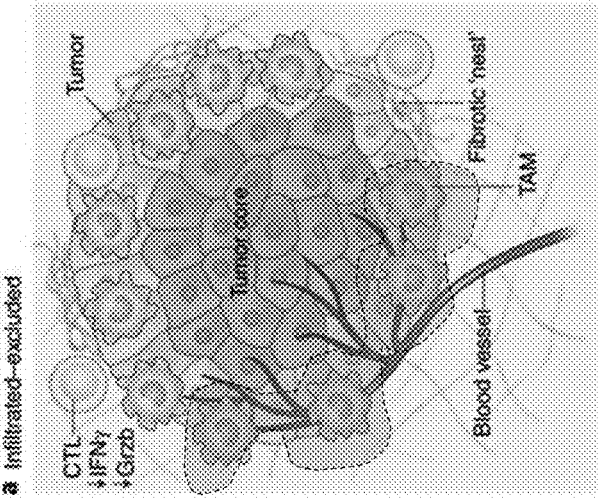
Figure 12B:
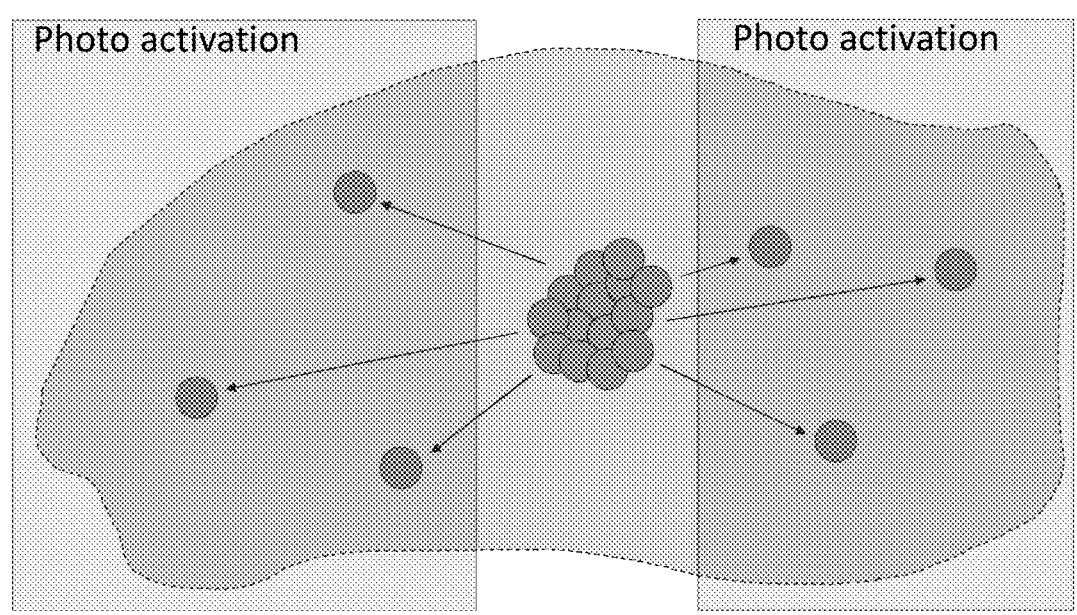
Figure 12C:
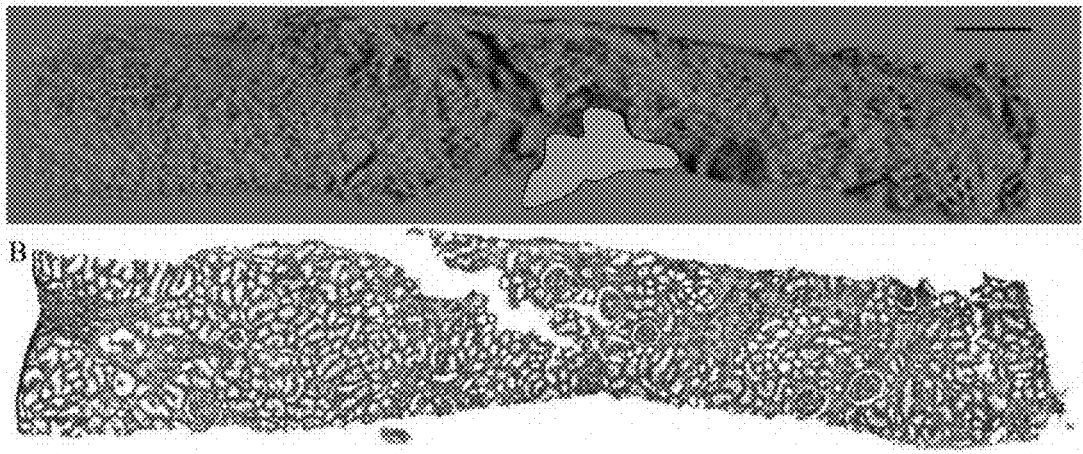

For the methods provided herein, in embodiments, the method further includes contacting the tissue or tissue sample with a second photo-activatable label and subjecting a second cell or nucleus in the tissue or tissue sample to a multi-photon laser, thereby labeling the second cell or nucleus. See, e.g., FIG. 11. In embodiments, the multi-photon laser is a two-photon laser. In embodiments, the multi-photon laser is a three-photon laser.

For the methods provided herein, in embodiments, the tissue or tissue sample is a whole organ, tumor, or animal. In embodiments, the tissue or tissue sample is a whole organ. In embodiments, the tissue or tissue sample is a tumor. In embodiments, the tissue or tissue sample is an animal. In embodiments, the tissue is a whole organ. In embodiments, the tissue is a tumor. In embodiments, the tissue is an animal. In embodiments, the tissue sample is a whole organ. In embodiments, the tissue sample is a tumor. In embodiments, the tissue sample is an animal.

For the methods provided herein, in embodiments, the wavelength of each photon in the two photon laser is between about 500 nm and about 1100 nm. In embodiments, the wavelength of each photon in the two photon laser is about 500 nm. In embodiments, the wavelength of each photon in the two photon laser is about 505 nm. In embodiments, the wavelength of each photon in the two photon laser is about 510 nm. In embodiments, the wavelength of each photon in the two photon laser is about 515 nm. In embodiments, the wavelength of each photon in the two photon laser is about 520 nm. In embodiments, the wavelength of each photon in the two photon laser is about 525 nm. In embodiments, the wavelength of each photon in the two photon laser is about 530 nm. In embodiments, the wavelength of each photon in the two photon laser is about 535 nm. In embodiments, the wavelength of each photon in the two photon laser is about 540 nm. In embodiments, the wavelength of each photon in the two photon laser is about 545 nm. In embodiments, the wavelength of each photon in the two photon laser is about 550 nm. In embodiments, the wavelength of each photon in the two photon laser is about 555 nm. In embodiments, the wavelength of each photon in the two photon laser is about 560 nm. In embodiments, the wavelength of each photon in the two photon laser is about 565 nm. In embodiments, the wavelength of each photon in the two photon laser is about 570 nm. In embodiments, the wavelength of each photon in the two photon laser is about 575 nm. In embodiments, the wavelength of each photon in the two photon laser is about 580 nm. In embodiments, the wavelength of each photon in the two photon laser is about 585 nm. In embodiments, the wavelength of each photon in the two photon laser is about 590 nm. In embodiments, the wavelength of each photon in the two photon laser is about 595 nm. In embodiments, the wavelength of each photon in the two photon laser is about 600 nm. In embodiments, the wavelength of each photon in the two photon laser is about 605 nm. In embodiments, the wavelength of each photon in the two photon laser is about 610 nm. In embodiments, the wavelength of each photon in the two photon laser is about 615 nm. In embodiments, the wavelength of each photon in the two photon laser is about 620 nm. In embodiments, the wavelength of each photon in the two photon laser is about 625 nm. In embodiments, the wavelength of each photon in the two photon laser is about 630 nm. In embodiments, the wavelength of each photon in the two photon laser is about 635 nm. In embodiments, the wavelength of each photon in the two photon laser is about 640 nm. In embodiments, the wavelength of each photon in the two photon laser is about 645 nm. In embodiments, the wavelength of each photon in the two photon laser is about 650 nm. In embodiments, the wavelength of each photon in the two photon laser is about 655 nm. In embodiments, the wavelength of each photon in the two photon laser is about 660 nm. In embodiments, the wavelength of each photon in the two photon laser is about 665 nm. In embodiments, the wavelength of each photon in the two photon laser is about 670 nm. In embodiments, the wavelength of each photon in the two photon laser is about 675 nm. In embodiments, the wavelength of each photon in the two photon laser is about 680 nm. In embodiments, the wavelength of each photon in the two photon laser is about 685 nm. In embodiments, the wavelength of each photon in the two photon laser is about 690 nm. In embodiments, the wavelength of each photon in the two photon laser is about 695 nm. In embodiments, the wavelength of each photon in the two photon laser is about 700 nm. In embodiments, the wavelength of each photon in the two photon laser is about 705 nm. In embodiments, the wavelength of each photon in the two photon laser is about 710 nm. In embodiments, the wavelength of each photon in the two photon laser is about 715 nm. In embodiments, the wavelength of each photon in the two photon laser is about 720 nm. In embodiments, the wavelength of each photon in the two photon laser is about 725 nm. In embodiments, the wavelength of each photon in the two photon laser is about 730 nm. In embodiments, the wavelength of each photon in the two photon laser is about 735 nm. In embodiments, the wavelength of each photon in the two photon laser is about 740 nm. In embodiments, the wavelength of each photon in the two photon laser is about 745 nm. In embodiments, the wavelength of each photon in the two photon laser is about 750 nm. In embodiments, the wavelength of each photon in the two photon laser is about 755 nm. In embodiments, the wavelength of each photon in the two photon laser is about 760 nm. In embodiments, the wavelength of each photon in the two photon laser is about 765 nm. In embodiments, the wavelength of each photon in the two photon laser is about 770 nm. In embodiments, the wavelength of each photon in the two photon laser is about 775 nm. In embodiments, the wavelength of each photon in the two photon laser is about 780 nm. In embodiments, the wavelength of each photon in the two photon laser is about 785 nm. In embodiments, the wavelength of each photon in the two photon laser is about 790 nm. In embodiments, the wavelength of each photon in the two photon laser is about 795 nm. In embodiments, the wavelength of each photon in the two photon laser is about 800 nm. In embodiments, the wavelength of each photon in the two photon laser is about 805 nm. In embodiments, the wavelength of each photon in the two photon laser is about 810 nm. In embodiments, the wavelength of each photon in the two photon laser is about 815 nm. In embodiments, the wavelength of each photon in the two photon laser is about 820 nm. In embodiments, the wavelength of each photon in the two photon laser is about 825 nm. In embodiments, the wavelength of each photon in the two photon laser is about 830 nm. In embodiments, the wavelength of each photon in the two photon laser is about 835 nm. In embodiments, the wavelength of each photon in the two photon laser is about 840 nm. In embodiments, the wavelength of each photon in the two photon laser is about 845 nm. In embodiments, the wavelength of each photon in the two photon laser is about 850 nm. In embodiments, the wavelength of each photon in the two photon laser is about 855 nm. In embodiments, the wavelength of each photon in the two photon laser is about 860 nm. In embodiments, the wavelength of each photon in the two photon laser is about 865 nm. In embodiments, the wavelength of each photon in the two photon laser is about 870 nm. In embodiments, the wavelength of each photon in the two photon laser is about 875 nm. In embodiments, the wavelength of each photon in the two photon laser is about 880 nm. In embodiments, the wavelength of each photon in the two photon laser is about 885 nm. In embodiments, the wavelength of each photon in the two photon laser is about 890 nm. In embodiments, the wavelength of each photon in the two photon laser is about 895 nm. In embodiments, the wavelength of each photon in the two photon laser is about 900 nm. In embodiments, the wavelength of each photon in the two photon laser is about 905 nm. In embodiments, the wavelength of each photon in the two photon laser is about 910 nm. In embodiments, the wavelength of each photon in the two photon laser is about 915 nm. In embodiments, the wavelength of each photon in the two photon laser is about 920 nm. In embodiments, the wavelength of each photon in the two photon laser is about 925 nm. In embodiments, the wavelength of each photon in the two photon laser is about 930 nm. In embodiments, the wavelength of each photon in the two photon laser is about 935 nm. In embodiments, the wavelength of each photon in the two photon laser is about 940 nm. In embodiments, the wavelength of each photon in the two photon laser is about 945 nm. In embodiments, the wavelength of each photon in the two photon laser is about 950 nm. In embodiments, the wavelength of each photon in the two photon laser is about 955 nm. In embodiments, the wavelength of each photon in the two photon laser is about 960 nm. In embodiments, the wavelength of each photon in the two photon laser is about 965 nm. In embodiments, the wavelength of each photon in the two photon laser is about 970 nm. In embodiments, the wavelength of each photon in the two photon laser is about 975 nm. In embodiments, the wavelength of each photon in the two photon laser is about 980 nm. In embodiments, the wavelength of each photon in the two photon laser is about 985 nm. In embodiments, the wavelength of each photon in the two photon laser is about 990 nm. In embodiments, the wavelength of each photon in the two photon laser is about 995 nm. In embodiments, the wavelength of each photon in the two photon laser is about 1000 nm. In embodiments, the wavelength of each photon in the two photon laser is about 1005 nm. In embodiments, the wavelength of each photon in the two photon laser is about 1010 nm. In embodiments, the wavelength of each photon in the two photon laser is about 1015 nm. In embodiments, the wavelength of each photon in the two photon laser is about 1020 nm. In embodiments, the wavelength of each photon in the two photon laser is about 1025 nm. In embodiments, the wavelength of each photon in the two photon laser is about 1030 nm. In embodiments, the wavelength of each photon in the two photon laser is about 1035 nm. In embodiments, the wavelength of each photon in the two photon laser is about 1040 nm. In embodiments, the wavelength of each photon in the two photon laser is about 1045 nm. In embodiments, the wavelength of each photon in the two photon laser is about 1050 nm. In embodiments, the wavelength of each photon in the two photon laser is about 1055 nm. In embodiments, the wavelength of each photon in the two photon laser is about 1060 nm. In embodiments, the wavelength of each photon in the two photon laser is about 1065 nm. In embodiments, the wavelength of each photon in the two photon laser is about 1070 nm. In embodiments, the wavelength of each photon in the two photon laser is about 1075 nm. In embodiments, the wavelength of each photon in the two photon laser is about 1080 nm. In embodiments, the wavelength of each photon in the two photon laser is about 1085 nm. In embodiments, the wavelength of each photon in the two photon laser is about 1090 nm. In embodiments, the wavelength of each photon in the two photon laser is about 1095 nm. In embodiments, the wavelength of each photon in the two photon laser is about 1100 nm. In embodiments, the wavelength of each photon in the two photon laser is about 905 nm, about 910 nm, about 915 nm, about 920 nm, about 925 nm, about 930 nm, about 935 nm, about 940 nm, about 945 nm, about 950 nm, about 955 nm, about 960 nm, about 965 nm, about 970 nm, about 975 nm, about 980 nm, about 985 nm, about 990 nm, about 995 nm, about 1000 nm, about 1005 nm, about 1010 nm, about 1015 nm, about 1020 nm, about 1025 nm, about 1030 nm, about 1035 nm, about 1040 nm, about 1045 nm, about 1050 nm, about 1055 nm, about 1060 nm, about 1065 nm, about 1070 nm, about 1075 nm, about 1080 nm, about 1085 nm, about 1090 nm, about 1095 nm, or about 1100 nm. The wavelength may be any value or subrange within the recited ranges, including endpoints, or any range between any of the recited values.

For the methods provided herein, in embodiments, the wavelength of each photon in a three photon laser is between about 690 nm and about 2500 nm. For the methods provided herein, in embodiments, the wavelength of each photon in a three photon laser is about 690 nm. In embodiments, the wavelength of each photon in a three photon laser is about 695 nm. In embodiments, the wavelength of each photon in a three photon laser is about 700 nm. In embodiments, the wavelength of each photon in a three photon laser is about 705 nm. In embodiments, the wavelength of each photon in a three photon laser is about 710 nm. In embodiments, the wavelength of each photon in a three photon laser is about 715 nm. In embodiments, the wavelength of each photon in a three photon laser is about 720 nm. In embodiments, the wavelength of each photon in a three photon laser is about 725 nm. In embodiments, the wavelength of each photon in a three photon laser is about 730 nm. In embodiments, the wavelength of each photon in a three photon laser is about 735 nm. In embodiments, the wavelength of each photon in a three photon laser is about 740 nm. In embodiments, the wavelength of each photon in a three photon laser is about 745 nm. In embodiments, the wavelength of each photon in a three photon laser is about 750 nm. In embodiments, the wavelength of each photon in a three photon laser is about 755 nm. In embodiments, the wavelength of each photon in a three photon laser is about 760 nm. In embodiments, the wavelength of each photon in a three photon laser is about 765 nm. In embodiments, the wavelength of each photon in a three photon laser is about 770 nm. In embodiments, the wavelength of each photon in a three photon laser is about 775 nm. In embodiments, the wavelength of each photon in a three photon laser is about 780 nm. In embodiments, the wavelength of each photon in a three photon laser is about 785 nm. In embodiments, the wavelength of each photon in a three photon laser is about 790 nm. In embodiments, the wavelength of each photon in a three photon laser is about 795 nm. In embodiments, the wavelength of each photon in a three photon laser is about 800 nm. In embodiments, the wavelength of each photon in a three photon laser is about 805 nm. In embodiments, the wavelength of each photon in a three photon laser is about 810 nm. In embodiments, the wavelength of each photon in a three photon laser is about 815 nm. In embodiments, the wavelength of each photon in a three photon laser is about 820 nm. In embodiments, the wavelength of each photon in a three photon laser is about 825 nm. In embodiments, the wavelength of each photon in a three photon laser is about 830 nm. In embodiments, the wavelength of each photon in a three photon laser is about 835 nm. In embodiments, the wavelength of each photon in a three photon laser is about 840 nm. In embodiments, the wavelength of each photon in a three photon laser is about 845 nm. In embodiments, the wavelength of each photon in a three photon laser is about 850 nm. In embodiments, the wavelength of each photon in a three photon laser is about 855 nm. In embodiments, the wavelength of each photon in a three photon laser is about 860 nm. In embodiments, the wavelength of each photon in a three photon laser is about 865 nm. In embodiments, the wavelength of each photon in a three photon laser is about 870 nm. In embodiments, the wavelength of each photon in a three photon laser is about 875 nm. In embodiments, the wavelength of each photon in a three photon laser is about 880 nm. In embodiments, the wavelength of each photon in a three photon laser is about 885 nm. In embodiments, the wavelength of each photon in a three photon laser is about 890 nm. In embodiments, the wavelength of each photon in a three photon laser is about 895 nm. In embodiments, the wavelength of each photon in a three photon laser is about 905 nm. In embodiments, the wavelength of each photon in a three photon laser is about 910 nm. In embodiments, the wavelength of each photon in a three photon laser is about 915 nm. In embodiments, the wavelength of each photon in a three photon laser is about 920 nm. In embodiments, the wavelength of each photon in a three photon laser is about 925 nm. In embodiments, the wavelength of each photon in a three photon laser is about 930 nm. In embodiments, the wavelength of each photon in a three photon laser is about 935 nm. In embodiments, the wavelength of each photon in a three photon laser is about 940 nm. In embodiments, the wavelength of each photon in a three photon laser is about 945 nm. In embodiments, the wavelength of each photon in a three photon laser is about 950 nm. In embodiments, the wavelength of each photon in a three photon laser is about 955 nm. In embodiments, the wavelength of each photon in a three photon laser is about 960 nm. In embodiments, the wavelength of each photon in a three photon laser is about 965 nm. In embodiments, the wavelength of each photon in a three photon laser is about 970 nm. In embodiments, the wavelength of each photon in a three photon laser is about 975 nm. In embodiments, the wavelength of each photon in a three photon laser is about 980 nm. In embodiments, the wavelength of each photon in a three photon laser is about 985 nm. In embodiments, the wavelength of each photon in a three photon laser is about 990 nm. In embodiments, the wavelength of each photon in a three photon laser is about 995 nm. In embodiments, the wavelength of each photon in a three photon laser is about 1000 nm. In embodiments, the wavelength of each photon in a three photon laser is about 1005 nm. In embodiments, the wavelength of each photon in a three photon laser is about 1010 nm. In embodiments, the wavelength of each photon in a three photon laser is about 1015 nm. In embodiments, the wavelength of each photon in a three photon laser is about 1020 nm. In embodiments, the wavelength of each photon in a three photon laser is about 1025 nm. In embodiments, the wavelength of each photon in a three photon laser is about 1030 nm. In embodiments, the wavelength of each photon in a three photon laser is about 1035 nm. In embodiments, the wavelength of each photon in a three photon laser is about 1040 nm. In embodiments, the wavelength of each photon in a three photon laser is about 1045 nm. In embodiments, the wavelength of each photon in a three photon laser is about 1050 nm. In embodiments, the wavelength of each photon in a three photon laser is about 1055 nm. In embodiments, the wavelength of each photon in a three photon laser is about 1060 nm. In embodiments, the wavelength of each photon in a three photon laser is about 1065 nm. In embodiments, the wavelength of each photon in a three photon laser is about 1070 nm. In embodiments, the wavelength of each photon in a three photon laser is about 1075 nm. In embodiments, the wavelength of each photon in a three photon laser is about 1080 nm. In embodiments, the wavelength of each photon in a three photon laser is about 1085 nm. In embodiments, the wavelength of each photon in a three photon laser is about 1090 nm. In embodiments, the wavelength of each photon in a three photon laser is about 1095 nm. In embodiments, the wavelength of each photon in a three photon laser is about 1100 nm. In embodiments, the wavelength of each photon in a three photon laser is about 1105 nm. In embodiments, the wavelength of each photon in a three photon laser is about 1110 nm. In embodiments, the wavelength of each photon in a three photon laser is about 1115 nm. In embodiments, the wavelength of each photon in a three photon laser is about 1120 nm. In embodiments, the wavelength of each photon in a three photon laser is about 1125 nm. In embodiments, the wavelength of each photon in a three photon laser is about 1130 nm. In embodiments, the wavelength of each photon in a three photon laser is about 1135 nm. In embodiments, the wavelength of each photon in a three photon laser is about 1140 nm. In embodiments, the wavelength of each photon in a three photon laser is about 1145 nm. In embodiments, the wavelength of each photon in a three photon laser is about 1150 nm. In embodiments, the wavelength of each photon in a three photon laser is about 1155 nm. In embodiments, the wavelength of each photon in a three photon laser is about 1160 nm. In embodiments, the wavelength of each photon in a three photon laser is about 1165 nm. In embodiments, the wavelength of each photon in a three photon laser is about 1170 nm. In embodiments, the wavelength of each photon in a three photon laser is about 1175 nm. In embodiments, the wavelength of each photon in a three photon laser is about 1180 nm. In embodiments, the wavelength of each photon in a three photon laser is about 1185 nm. In embodiments, the wavelength of each photon in a three photon laser is about 1190 nm. In embodiments, the wavelength of each photon in a three photon laser is about 1195 nm. In embodiments, the wavelength of each photon in a three photon laser is about 2000 nm. In embodiments, the wavelength of each photon in a three photon laser is about 2005 nm. In embodiments, the wavelength of each photon in a three photon laser is about 2010 nm. In embodiments, the wavelength of each photon in a three photon laser is about 2015 nm. In embodiments, the wavelength of each photon in a three photon laser is about 2020 nm. In embodiments, the wavelength of each photon in a three photon laser is about 2025 nm. In embodiments, the wavelength of each photon in a three photon laser is about 2030 nm. In embodiments, the wavelength of each photon in a three photon laser is about 2035 nm. In embodiments, the wavelength of each photon in a three photon laser is about 2040 nm. In embodiments, the wavelength of each photon in a three photon laser is about 2045 nm. In embodiments, the wavelength of each photon in a three photon laser is about 2050 nm. In embodiments, the wavelength of each photon in a three photon laser is about 2055 nm. In embodiments, the wavelength of each photon in a three photon laser is about 2060 nm. In embodiments, the wavelength of each photon in a three photon laser is about 2065 nm. In embodiments, the wavelength of each photon in a three photon laser is about 2070 nm. In embodiments, the wavelength of each photon in a three photon laser is about 2075 nm. In embodiments, the wavelength of each photon in a three photon laser is about 2080 nm. In embodiments, the wavelength of each photon in a three photon laser is about 2085 nm. In embodiments, the wavelength of each photon in a three photon laser is about 2090 nm. In embodiments, the wavelength of each photon in a three photon laser is about 2100 nm. In embodiments, the wavelength of each photon in a three photon laser is about 2105 nm. In embodiments, the wavelength of each photon in a three photon laser is about 2110 nm. In embodiments, the wavelength of each photon in a three photon laser is about 2115 nm. In embodiments, the wavelength of each photon in a three photon laser is about 2120 nm. In embodiments, the wavelength of each photon in a three photon laser is about 2125 nm. In embodiments, the wavelength of each photon in a three photon laser is about 2130 nm. In embodiments, the wavelength of each photon in a three photon laser is about 2135 nm. In embodiments, the wavelength of each photon in a three photon laser is about 2140 nm. In embodiments, the wavelength of each photon in a three photon laser is about 2145 nm. In embodiments, the wavelength of each photon in a three photon laser is about 2150 nm. In embodiments, the wavelength of each photon in a three photon laser is about 2155 nm. In embodiments, the wavelength of each photon in a three photon laser is about 2160 nm. In embodiments, the wavelength of each photon in a three photon laser is about 2165 nm. In embodiments, the wavelength of each photon in a three photon laser is about 2170 nm. In embodiments, the wavelength of each photon in a three photon laser is about 2175 nm. In embodiments, the wavelength of each photon in a three photon laser is about 2180 nm. In embodiments, the wavelength of each photon in a three photon laser is about 2185 nm. In embodiments, the wavelength of each photon in a three photon laser is about 2190 nm. In embodiments, the wavelength of each photon in a three photon laser is about 2195 nm. In embodiments, the wavelength of each photon in a three photon laser is about 2200 nm. In embodiments, the wavelength of each photon in a three photon laser is about 2205 nm. In embodiments, the wavelength of each photon in a three photon laser is about 2210 nm. In embodiments, the wavelength of each photon in a three photon laser is about 2215 nm. In embodiments, the wavelength of each photon in a three photon laser is about 2220 nm. In embodiments, the wavelength of each photon in a three photon laser is about 2225 nm. In embodiments, the wavelength of each photon in a three photon laser is about 2230 nm. In embodiments, the wavelength of each photon in a three photon laser is about 2235 nm. In embodiments, the wavelength of each photon in a three photon laser is about 2240 nm. In embodiments, the wavelength of each photon in a three photon laser is about 2245 nm. In embodiments, the wavelength of each photon in a three photon laser is about 2250 nm. In embodiments, the wavelength of each photon in a three photon laser is about 2255 nm. In embodiments, the wavelength of each photon in a three photon laser is about 2260 nm. In embodiments, the wavelength of each photon in a three photon laser is about 2265 nm. In embodiments, the wavelength of each photon in a three photon laser is about 2270 nm. In embodiments, the wavelength of each photon in a three photon laser is about 2275 nm. In embodiments, the wavelength of each photon in a three photon laser is about 2280 nm. In embodiments, the wavelength of each photon in a three photon laser is about 2285 nm. In embodiments, the wavelength of each photon in a three photon laser is about 2290 nm. In embodiments, the wavelength of each photon in a three photon laser is about 2295 nm. In embodiments, the wavelength of each photon in a three photon laser is about 2300 nm. In embodiments, the wavelength of each photon in a three photon laser is about 2305 nm. In embodiments, the wavelength of each photon in a three photon laser is about 2310 nm. In embodiments, the wavelength of each photon in a three photon laser is about 2315 nm. In embodiments, the wavelength of each photon in a three photon laser is about 2320 nm. In embodiments, the wavelength of each photon in a three photon laser is about 2325 nm. In embodiments, the wavelength of each photon in a three photon laser is about 2330 nm. In embodiments, the wavelength of each photon in a three photon laser is about 2335 nm. In embodiments, the wavelength of each photon in a three photon laser is about 2340 nm. In embodiments, the wavelength of each photon in a three photon laser is about 2345 nm. In embodiments, the wavelength of each photon in a three photon laser is about 2350 nm. In embodiments, the wavelength of each photon in a three photon laser is about 2350 nm. In embodiments, the wavelength of each photon in a three photon laser is about 2355 nm. In embodiments, the wavelength of each photon in a three photon laser is about 2360 nm. In embodiments, the wavelength of each photon in a three photon laser is about 2365 nm. In embodiments, the wavelength of each photon in a three photon laser is about 2370 nm. In embodiments, the wavelength of each photon in a three photon laser is about 2375 nm. In embodiments, the wavelength of each photon in a three photon laser is about 2380 nm. In embodiments, the wavelength of each photon in a three photon laser is about 2385 nm. In embodiments, the wavelength of each photon in a three photon laser is about 2390 nm. In embodiments, the wavelength of each photon in a three photon laser is about 2395 nm. In embodiments, the wavelength of each photon in a three photon laser is about 2400 nm. In embodiments, the wavelength of each photon in a three photon laser is about 2405 nm. In embodiments, the wavelength of each photon in a three photon laser is about 2410 nm. In embodiments, the wavelength of each photon in a three photon laser is about 2415 nm. In embodiments, the wavelength of each photon in a three photon laser is about 2420 nm. In embodiments, the wavelength of each photon in a three photon laser is about 2425 nm. In embodiments, the wavelength of each photon in a three photon laser is about 2430 nm. In embodiments, the wavelength of each photon in a three photon laser is about 2435 nm. In embodiments, the wavelength of each photon in a three photon laser is about 2440 nm. In embodiments, the wavelength of each photon in a three photon laser is about 2445 nm. In embodiments, the wavelength of each photon in a three photon laser is about 2450 nm. In embodiments, the wavelength of each photon in a three photon laser is about 2455 nm. In embodiments, the wavelength of each photon in a three photon laser is about 2460 nm. In embodiments, the wavelength of each photon in a three photon laser is about 2465 nm. In embodiments, the wavelength of each photon in a three photon laser is about 2470 nm. In embodiments, the wavelength of each photon in a three photon laser is about 2475 nm. In embodiments, the wavelength of each photon in a three photon laser is about 2480 nm. In embodiments, the wavelength of each photon in a three photon laser is about 2485 nm. In embodiments, the wavelength of each photon in a three photon laser is about 2490 nm. In embodiments, the wavelength of each photon in a three photon laser is about 2495 nm. In embodiments, the wavelength of each photon in a three photon laser is about 2500 nm.

Compositions

In an aspect is provided a composition. The composition may include a tissue sample, a medium having a refraction index similar to or matching the tissue, and a photo-activatable label. In embodiments, the tissue includes a labeled region. In embodiments, the region includes a cell, a subcellular compartment, an aggregate, or a secreted aggregate. In embodiments, the region includes a cell. In embodiments, the region includes a subcellular compartment. In embodiments, the region includes an aggregate. In embodiments, the region includes a secreted aggregate. In embodiments, the cell was labeled by a multi-photon method. In embodiments, the cell was labeled by a two-photon method. In embodiments, the cell was labeled by a three-photon method. In embodiments, the photo-activatable label includes a detectable moiety. In embodiments, the detectable moiety includes a light emitting moiety. In embodiments, the light emitting moiety is a fluorescent moiety, a chemiluminescent moiety, a bioluminescent moiety, or an electrochemiluminescent moiety. In embodiments, the light emitting moiety is a fluorescent moiety. In embodiments, the light emitting moiety is a chemiluminescent moiety. In embodiments, the light emitting moiety is a bioluminescent moiety. In embodiments, the light emitting moiety is an electrochemiluminescent moiety. In embodiments, the fluorescent moiety includes a fluorophore.

For the compositions provided herein, in embodiments, the photo-activatable label includes a tag. In embodiments, the tag is chosen from the group including an affinity tag, an epitope tag, a fluorescent tag, an oligonucleotide tag, or a biotin tag. In embodiments, the tag is an affinity tag. In embodiments, the tag is an epitope tag. In embodiments, the tag is a fluorescent tag. In embodiments, the tag is an oligonucleotide tag. In embodiments, the tag is a biotin tag. In embodiments, the detectable moiety is an antibody or a functional derivative thereof. In embodiments, the photo-activatable label is hydrophobic.

For the compositions provided herein, in embodiments, the photo-activatable label includes a phenyl azide group, an ortho-hydroxyphenyl azide group, a meta-hydroxyphenyl azide group, a tertrafluorophenyl azide group, an ortho-nitrophenyl azide group, a meta-nitrophenyl azide group, a diazirine group, an azido-methylcoumarin group, or a psoralen group. In embodiments, the photo-activatable label includes a phenyl azide group. In embodiments, the photo-activatable label includes an ortho-hydroxyphenyl azide group. In embodiments, the photo-activatable label includes a meta-hydroxyphenyl azide group. In embodiments, the photo-activatable label includes a tertrafluorophenyl azide group. In embodiments, the photo-activatable label includes an ortho-nitrophenyl azide group. In embodiments, the photo-activatable label includes a meta-nitrophenyl azide group. In embodiments, the photo-activatable label includes a diazirine group. In embodiments, the photo-activatable label includes an azido-methylcoumarin group. In embodiments, the photo-activatable label includes a psoralen group.

For the compositions provided herein, in embodiments, the medium includes a solution of Benzyl Alcohol, Benzyl Benzoate (BABB) or derivatives thereof, with or without one or more of triethylamine, diphenyl ether, dibenzyl ether, α-tocopherol, and/or Quadrol. In embodiments, the medium includes a solution of Benzyl Alcohol with one or more of triethylamine, diphenyl ether, dibenzyl ether, α-tocopherol, and/or Quadrol. In embodiments, the medium includes a solution of Benzyl Alcohol without one or more of triethylamine, diphenyl ether, dibenzyl ether, α-tocopherol, and/or Quadrol. In embodiments, the medium includes a solution of Benzyl Benzoate (BABB) or derivatives thereof, with one or more of triethylamine, diphenyl ether, dibenzyl ether, α-tocopherol, and/or Quadrol. In embodiments, the medium includes a solution of Benzyl Benzoate (BABB) or derivatives thereof, without one or more of triethylamine, diphenyl ether, dibenzyl ether, α-tocopherol, and/or Quadrol. In embodiments, the medium includes a BABB solution. In embodiments, one or more of the listed components may be expressly excluded.

In an aspect is provided a cleared tissue sample. The cleared issue sample may include a photo-activatable label and a medium having a refraction index substantially matching the index of the tissue. In embodiments, for the cleared tissue provided herein, the medium includes a solution of Benzyl Alcohol, Benzyl Benzoate (BABB) or derivatives thereof, with or without one or more of triethylamine, diphenyl ether, dibenzyl ether, α-tocopherol, and/or Quadrol. In embodiments, the medium includes a solution of Benzyl Alcohol with one or more of triethylamine, diphenyl ether, dibenzyl ether, α-tocopherol, and/or Quadrol. In embodiments, the medium includes a solution of Benzyl Alcohol without one or more of triethylamine, diphenyl ether, dibenzyl ether, α-tocopherol, and/or Quadrol. In embodiments, the medium includes a solution of Benzyl Benzoate (BABB) or derivatives thereof, with one or more of triethylamine, diphenyl ether, dibenzyl ether, α-tocopherol, and/or Quadrol. In embodiments, the medium includes a solution of Benzyl Benzoate (BABB) or derivatives thereof, without one or more of triethylamine, diphenyl ether, dibenzyl ether, α-tocopherol, and/or Quadrol. In embodiments, the medium includes a BABB solution. In embodiments, one or more of the listed components may be expressly excluded.

In embodiments, the cleared tissue provided here includes a labeled cell. In embodiments, the cell was labeled by a multi-photon method. In embodiments, the photo-activatable label includes a detectable moiety. In embodiments, the detectable moiety includes a light emitting moiety. In embodiments, the light emitting moiety is a fluorescent moiety, a chemiluminescent moiety, a bioluminescent moiety, or an electrochemiluminescent moiety. In embodiments, the light emitting moiety is a fluorescent moiety. In embodiments, the light emitting moiety is a chemiluminescent moiety. In embodiments, the light emitting moiety is a bioluminescent moiety. In embodiments, the light emitting moiety is an electrochemiluminescent moiety. In embodiments, the fluorescent moiety includes a fluorophore. In embodiments, the photo-activatable label includes a tag. In embodiments, the tag is chosen from the group including an affinity tag, an epitope tag, a fluorescent tag, an oligonucleotide tag, or a biotin tag. In embodiments, the tag is an affinity tag. In embodiments, the tag is an epitope tag. In embodiments, the tag is a fluorescent tag. In embodiments, the tag is an oligonucleotide tag. In embodiments, the tag is a biotin tag. In embodiments, the detectable moiety is an antibody or a functional derivative thereof. In embodiments, the photo-activatable label is hydrophobic. In embodiments, one or more of the listed labels may be expressly excluded.

For the cleared tissue provided herein, in embodiments, the photo-activatable label includes a phenyl azide group, an ortho-hydroxyphenyl azide group, a meta-hydroxyphenyl azide group, a tertrafluorophenyl azide group, an ortho-nitrophenyl azide group, a meta-nitrophenyl azide group, a diazirine group, an azido-methylcoumarin group, or a psoralen group. In embodiments, the photo-activatable label includes a phenyl azide group. In embodiments, the photo-activatable label includes an ortho-hydroxyphenyl azide group. In embodiments, the photo-activatable label includes a meta-hydroxyphenyl azide group. In embodiments, the photo-activatable label includes a tertrafluorophenyl azide group. In embodiments, the photo-activatable label includes an ortho-nitrophenyl azide group. In embodiments, the photo-activatable label includes a meta-nitrophenyl azide group. In embodiments, the photo-activatable label includes a diazirine group. In embodiments, the photo-activatable label includes an azido-methylcoumarin group. In embodiments, the photo-activatable label includes a psoralen group. In embodiments, one or more of the listed labels may be expressly excluded.

Uses

The methods and compositions described herein can be used in any application where a three-dimensional tissue analysis is desired. The following uses are examples only, and are not intended to be limiting.

In embodiments, the compositions and methods described herein may be used to detect heterogeneity in a tumor or tumor sample (e.g., biopsy). A tumor sample from a patient may be cleared as described herein. The tumor sample may then be contacted with a photo-activatable label and one or more regions of interest subjected to a multi-photon laser (e.g., 2-photon laser). Regions of interest may include various regions within the tumor, as well as tumor-adjacent "normal" cells. The labeled region(s) can be isolated and analyzed by one or more methods of analysis, e.g. DNA, RNA, and/or protein analysis. The tumor sample may be imaged at any step or multiple steps prior to isolation or analysis, for example before or after clearing, before or after contact with the photo-activatable label, etc. The DNA, RNA and/or protein profile determined from the analysis can be combined with the image to provide a detailed map of the tumor. Analysis of tumor DNA, RNA and/or protein within various regions may allow for the construction of a 3-dimensional evolutionary model of tumor heterogeneity.

In embodiments, the compositions and methods described herein may be used to identify immune cells (or lack thereof) in a sample, for example a tumor sample. For example, one or more regions of a sample may be labeled, imaged, and isolated, as described herein. The isolated regions can be analyzed, e.g. for RNA and/or protein that is expressed (preferentially expressed) by one or more immune cells of interest.

In embodiments, the compositions and methods described herein may be used to identify the location of blood vessels, and/or to analyze DNA, or RNA or protein expression based on proximity to blood vessels, in a sample, for example a tumor sample. For example, one or more regions of a sample may be labeled, imaged, and isolated, as described herein, based on the proximity to blood vessels. The isolated regions can be analyzed, e.g. for RNA and/or protein that is expressed (preferentially expressed) by one or more cells of interest. Similarly, regions of metastasis or suspected metastasis can be analyzed using these methods.

In embodiments, the compositions and methods described herein may be used to find locations of sparse populations of cells. Some cell types are found in low numbers in certain tissues, and/or are dispersed in discrete areas within a tissue. The compositions and methods described herein may help to identify/locate those cells or regions within a tissue.

In embodiments, the compositions and methods described herein may be used to profile particular cell types in a sample. For example, and without limitation, the spinal cord is comprised of multiple layers/regions of dorsal root ganglia, each layer or region containing different cell types. The compositions and methods described herein may help to identify differences (and/or similarities) between cells in the various layers. Thus, any tissue comprised of multiple cell types could be analyzed.

In embodiments, the compositions and methods described herein may be used to generate data, e.g. expression (e.g., RNA or protein) or mutation (e.g., DNA) data, for a region of interest in a tissue or sample after analysis of the tissue or sample with 3D histology.

In embodiments, the compositions and methods described herein may be used to label and extract precise regions of interest within a tissue or sample. For example, a region of interest could be labeled within a resolution of $1.6 \times 1.6 \times 3$ µm (using a 20× lens).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

One skilled in the art would understand that descriptions of making and using the particles described herein is for the sole purpose of illustration, and that the present disclosure is not limited by this illustration.

Example 1

Dehydration and Clearing of Tissue

Dehydration and Tissue Clearing

In order to harvest organs void of residual blood, mice were perfused with warm PBS/Heparin (5U/ml; 50-100 ml per mouse at steady pressure (gravity flow or Perfusion One system; 1-1.5 mH2O(Leica))) followed by perfusion with PFA 2% (Electron Microscopy Sciences, diluted in PBS). Depending on sample permeability, removed organs were subjected to a post fixation in PFA overnight at 4° C. Samples were incubated for X h each (where X is the time determined by Fick's law of diffusion with a mouse brain incubated for 24h serving as a reference; $T=(1/[2D])r^2$, D=diffusion coefficient (inferred from mouse brain dimension and incubation time =0.00015349), r=closest distance to sample center) in 30% and 50% tert-Butanol (pH=9.5, RT), subsequently in 70%, 80%, 96% and 100% tert-Butanol (pH=9.5, 30° C.), sequentially, and finally cleared in BABB (benzyl-alcohol:benzyl benzoate in a 1:2 volume ratio, pH=9.5, 30° C.). After the final clearing step, the organ can be stored in BABB solution for at least one year at 4° C. An example of cleared mouse brain following this protocol, with approximately 24 h incubation per step, can be found on FIG. 1.

Stability Experiments

Figure 2:
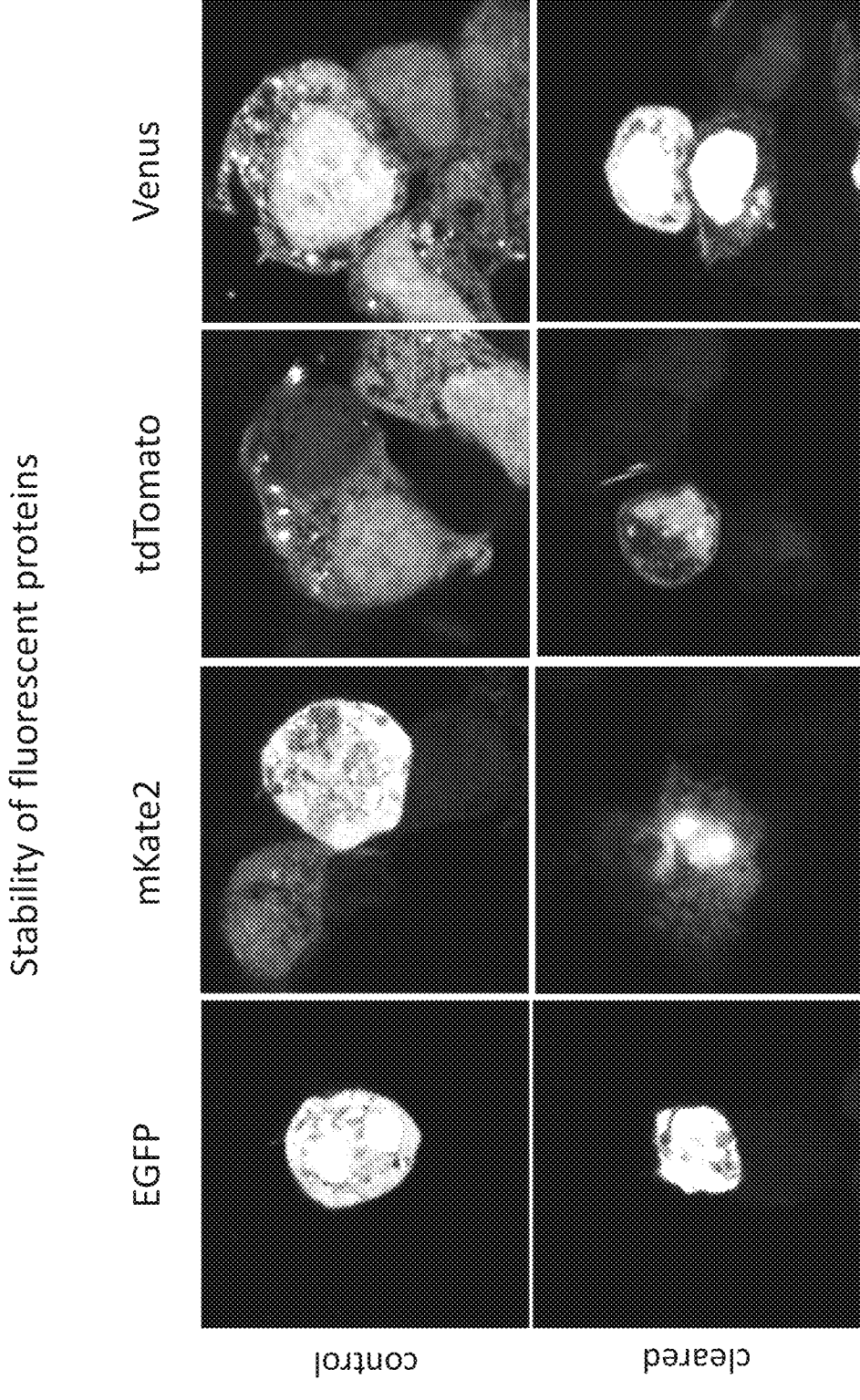
FIG. 2 is a series of fluorescence microscopy pictures showing the stability of different fluorescent proteins in cleared tissue (bottom row) or control tissue (top row). In this figure, 293T cells were transfected with plasmids driving the expression of EGFP, mKate2, tdTomato or Venus under control of the CMV promoter, respectively.
Figure 3B:
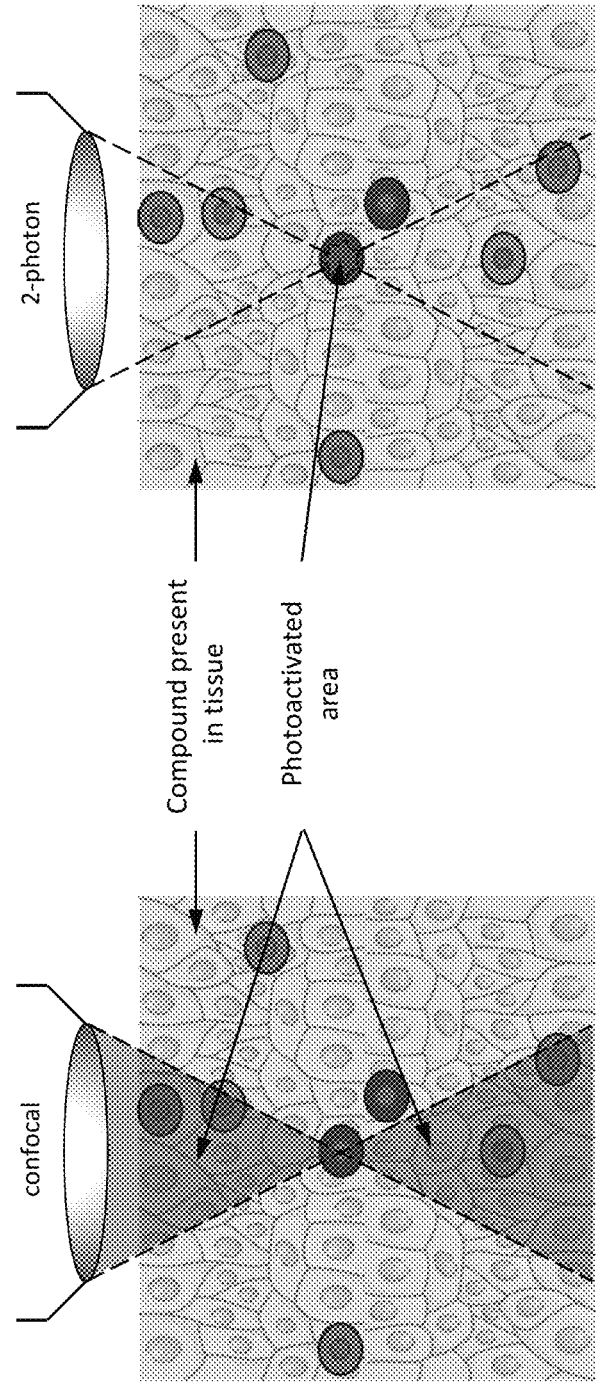
Figure 4:
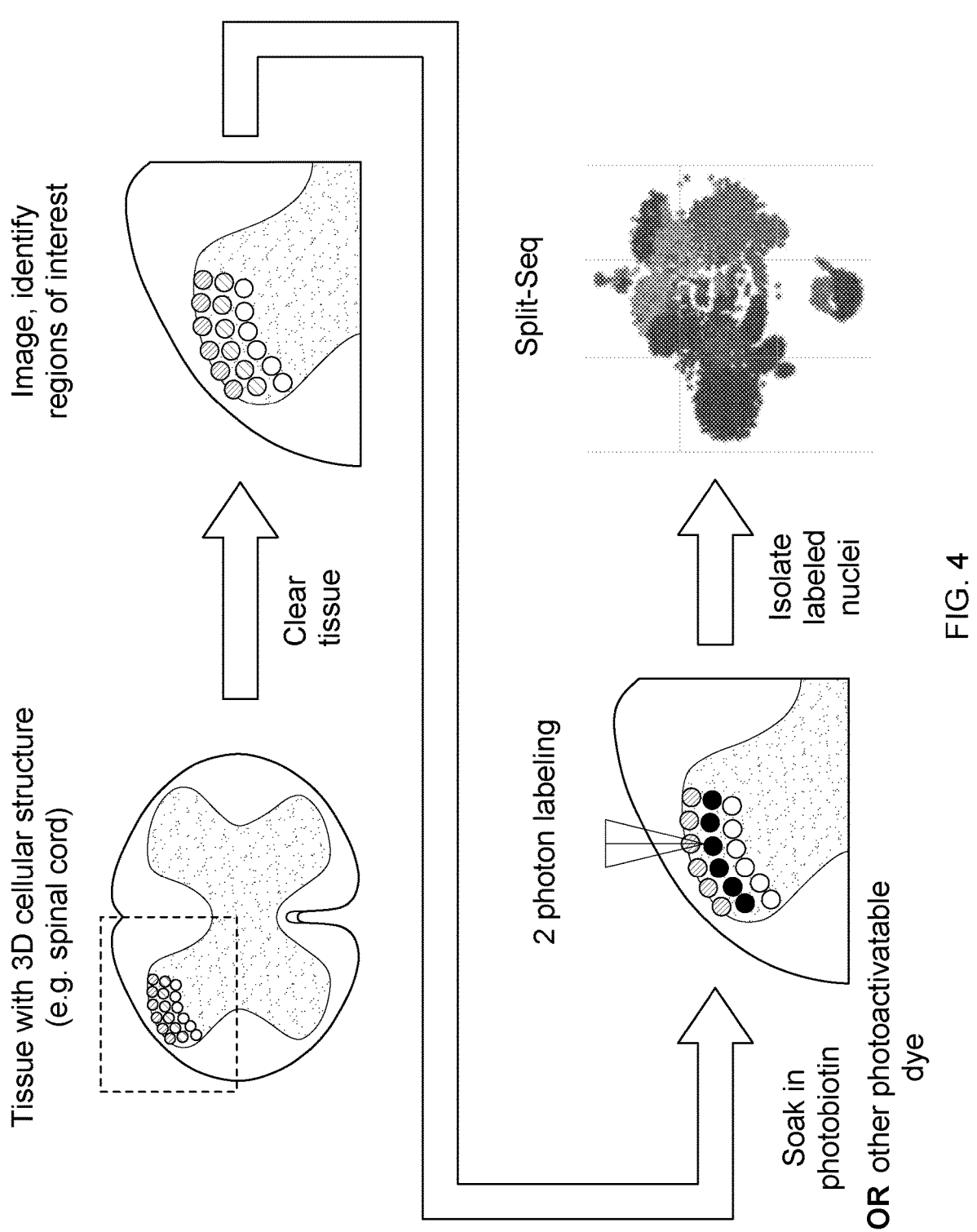
FIG. 4 presents an overview of an example analysis using the two-photon labeling technology. Tissue with a three-dimensional (3D) cellular structure is cleared, soaked in a photoactivatable dye (e.g., photobiotin), labeled using a 2-photon laser (e.g., as shown in FIG. 3B), followed by isolation of the labeled nuclei for analysis, for example single cell analysis (e.g., SPLiT-seq).
Figure 5:
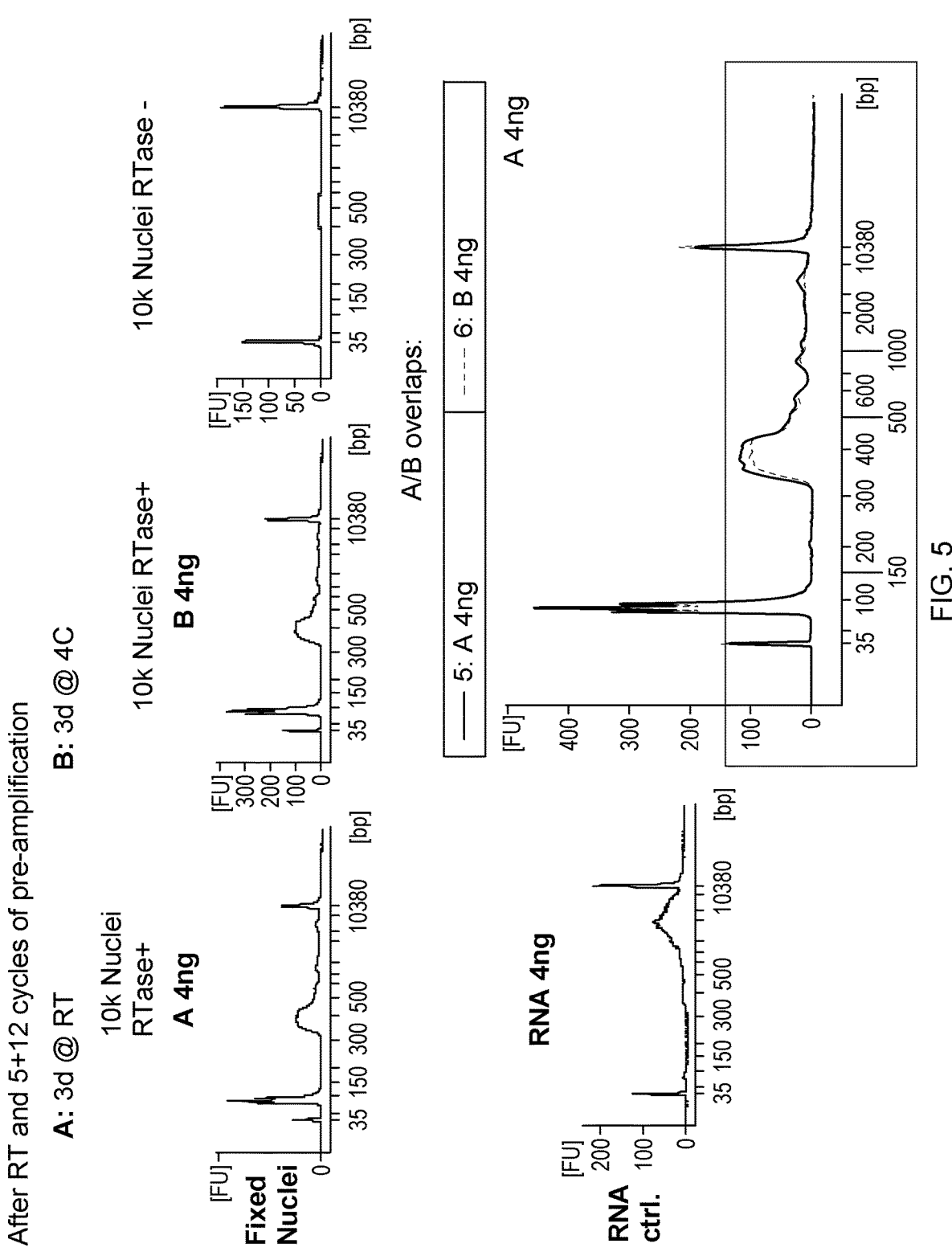
FIG. 5 shows polynucleotide length profiles for treated samples without EDC treatment after three days at room temperature (RT) or 4° C. (4C), following reverse transcription.
Figure 6A:
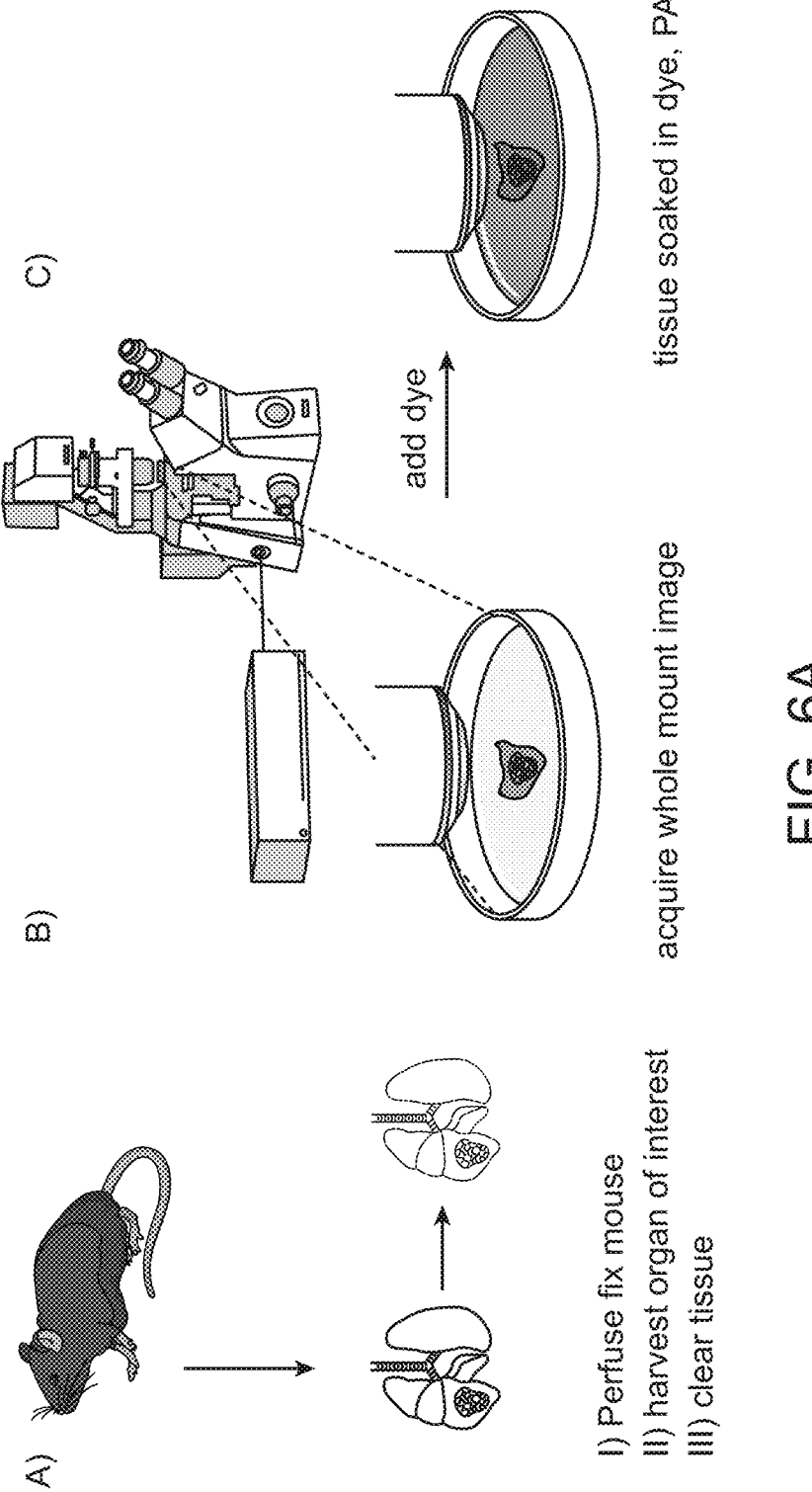
FIGS. 6A-6C present an overview of a method of spatial-dependent analysis of biological material from intact tissue samples.
Figure 6A:
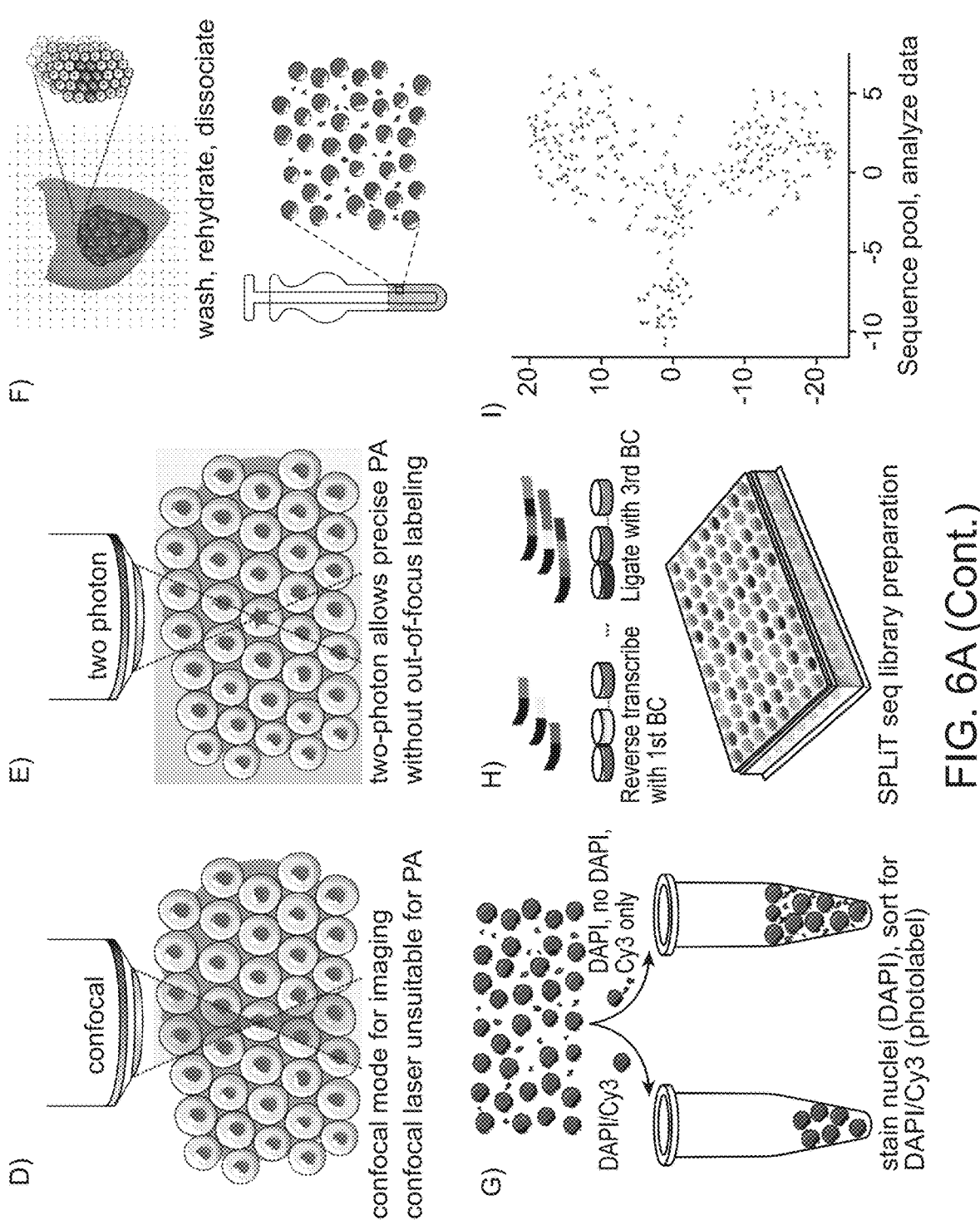
Figures 6B, 6C:
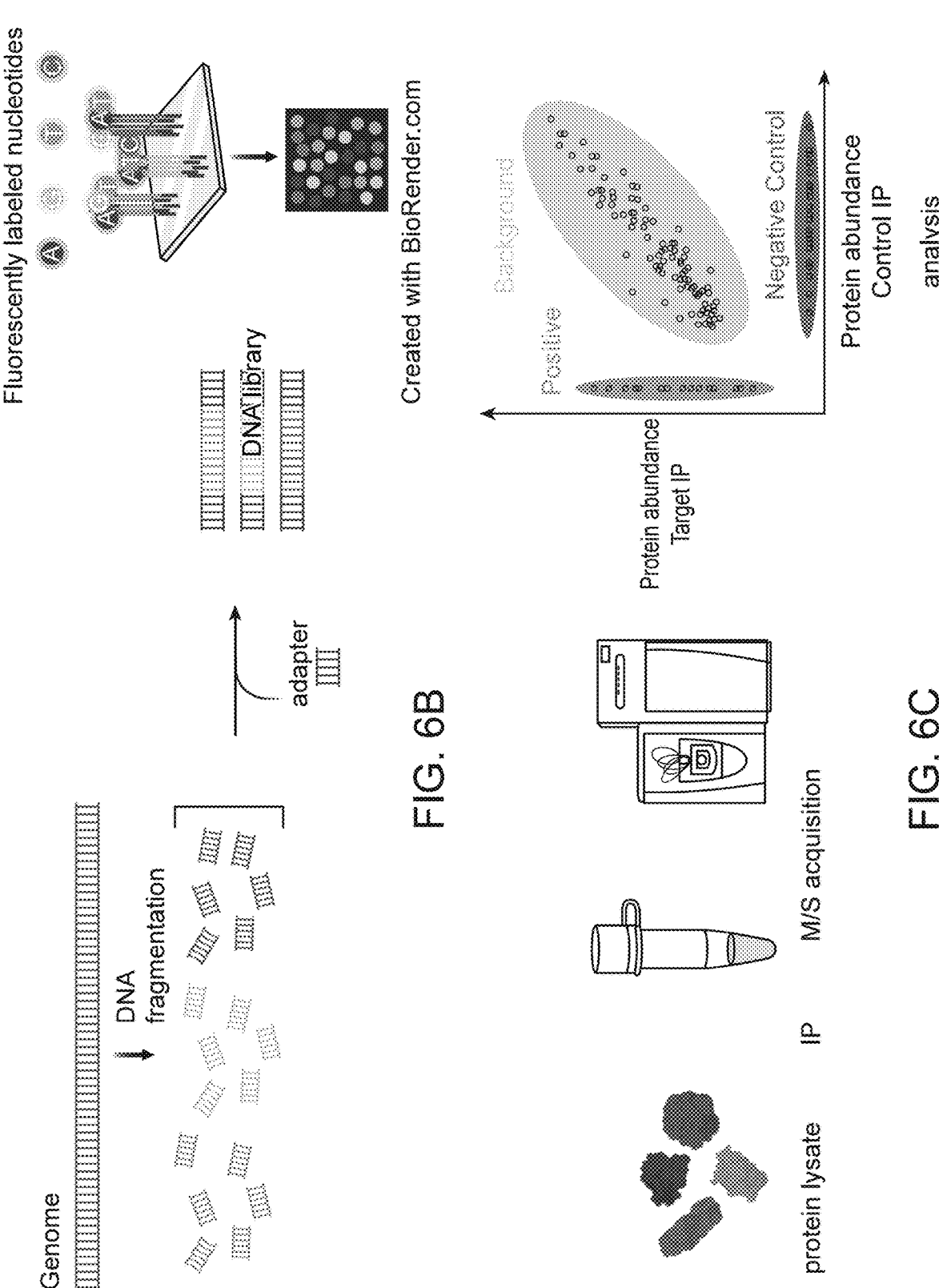

In order to show that the above described protocol did not alter the stability and integrity of cells, HEK293 cells were transfected with plasmids coding for EGFP, mKate2, tdTomato or Venus, respectively. Cells were plated on Millipore EZ slides, fixed with PFA 4% and then treated following the protocol described above, with an incubation time per step of 15 min. For mounting, BABB was used as mounting media and a glass cover slip was used to cover the cells. Cells were then imaged using a Leica SP8 upright laser scanning microscope with wavelengths matching the excitation/emission spectra of the fluorescent proteins. Control slides were not subjected to the clearing protocol and mounted using VectaShield mounting media. Exemplary results of these stability experiments are shown in FIG. 2.

Example 2

Two-photon Labeling of Tissue

For spatially-defined activation of photoreactive compounds deep within tissue, samples were incubated with suitable compounds dissolved in BABB (12.5 µg/ml) for the times described by Fick's law of diffusion at room temperature (RT), or overnight at 4° C. Successful conjugation of the compound to the site of interest was achieved by using a pixel dwell time of 10 µs for a resolution of 512×512 with a 20× lens (Leica HCX APO L 20×/0.95 IMM) and 75 mW of laser power at the lens at 700 nm. Based on the composition of photobiotin (biotin-linker-phenylazide; Sigma A1935-1MG), photoactivatable Pacific blue, Cy3, Cy5 and Alexa 488 were synthesized that are readily dissolvable in pH-adjusted BABB at 1 mg/ml (stock concentration). Immediately after photo labeling of the samples, samples were washed (by transferring the sample into the respective solution) for the time determined by Fick's law in BABB (pH=9.5, 30° C.), then in 100% tert-Butanol (pH=9.5, 30° C.), followed by a final washing step in 100% DMSO (pH=9.5, 30° C.) and subsequently stored at 4° C. in 100% DMSO until further processed.

Example 3

Isolation and Purification of Photo Labeled Nuclei

All equipment was treated with RNAse away. Photo labelled tissue stored in DMSO was rehydrated by incubation in PBS supplemented with RNAse inhibitor (Takara) on a shaker at 20° C. for 30 min. The tissue was chopped into <1 mm bits and transferred to Lysis buffer (975 µl HBSS containing divalents, 10 µl proteinase K, 10 µl RNAse-free DNAse, and 0.2 U/ml RNAse inhibitor). Following an incubation for 15 min at 30° C., the tissue bits were transferred to a Dounce homogenizer and 1 ml of HBSS+ solution (HBSS, 3% BSA (fatty acid free) and 0.2U/ml RNAse inhibitor) was added before homogenizing by 5-10 strokes (avoiding bubbles). The homogenate was filtered through a prewetted 70 µm filter and spun at 300 rcf for 3-5 min. The supernatant was discarded, the pellet resuspended in HBSS+, triturated with a 200 µl tip to break up nuclei clumps, pelleted at 300 rcf, resuspended in 1 ml HBSS+and mixed with an equal volume of cold 25% Optiprep (Sigma-Aldrich) before placing on ice. On ice a gradient was prepared in a 15 ml tube by adding 2 ml of 40% Optiprep to the bottom, pipetting 2 ml of 25% Optiprep on top and carefully layering the nuclei mixture over it. The tube then was spun in a pre-cooled swinging bucket rotor at 2500 rcf for 20 min. The nuclei located at the interface of the 25% and the 40% Optiprep solution (located under the fluffy opaque layer of debris, might appear transparent with a brownish hue) were collected and resuspend in 3 volumes of HBSS+ before spinning at 250 rcf for 10 min. The pellet then was washed with HBSS+ before resuspending it in HBSS+ and adding appropriate nuclei label for FACS (PI or DAPI) or a Streptavidin-linked dye to stain for biotin incorporation. Following a 5 min incubation at RT, the sample was spun down and resuspended in HBSS+. For sorting prepare an unlabeled control that was treated identical to the sample except being exposed to light that was used for photoactivation and gate for single nuclei (using nuclei label) and photo labeled nuclei.

Example 4

Image Acquisition and Analysis

Cleared samples were mounted on insect pins (Austerlitz) that were fixed to an inert silicone rubber surface (Momentive, RTV615), completely covered with BABB and imaged using a Leica SP8 microscope equipped with a white light laser and Leica BABB immersion lenses HCX PL FLUOTAR 5×/0.15 IMM lens for low-resolution and HCX APO L 20×/0.95 IMM lens for high resolution. Acquired Leica image containers were converted to Imaris containers (Imaris File Converter 9.1.2, Bitplane) and transferred to a power workstation (Dual Xeon ES-2687W v4, 1TB memory, GeForce Titan (Pascal)) for image analysis using Imaris 9.3.1 (Bitplane). When necessary, signal intensity was compensated using a non-signal channel and the adapthresh function from Matlab (MathWorks) or image data was deconvolved using Huygens (Scientific Volume Imaging B.V.).

Example 5

SPLiT-seq of Cleared Nuclei from Spinal Cord

Figure 7A:
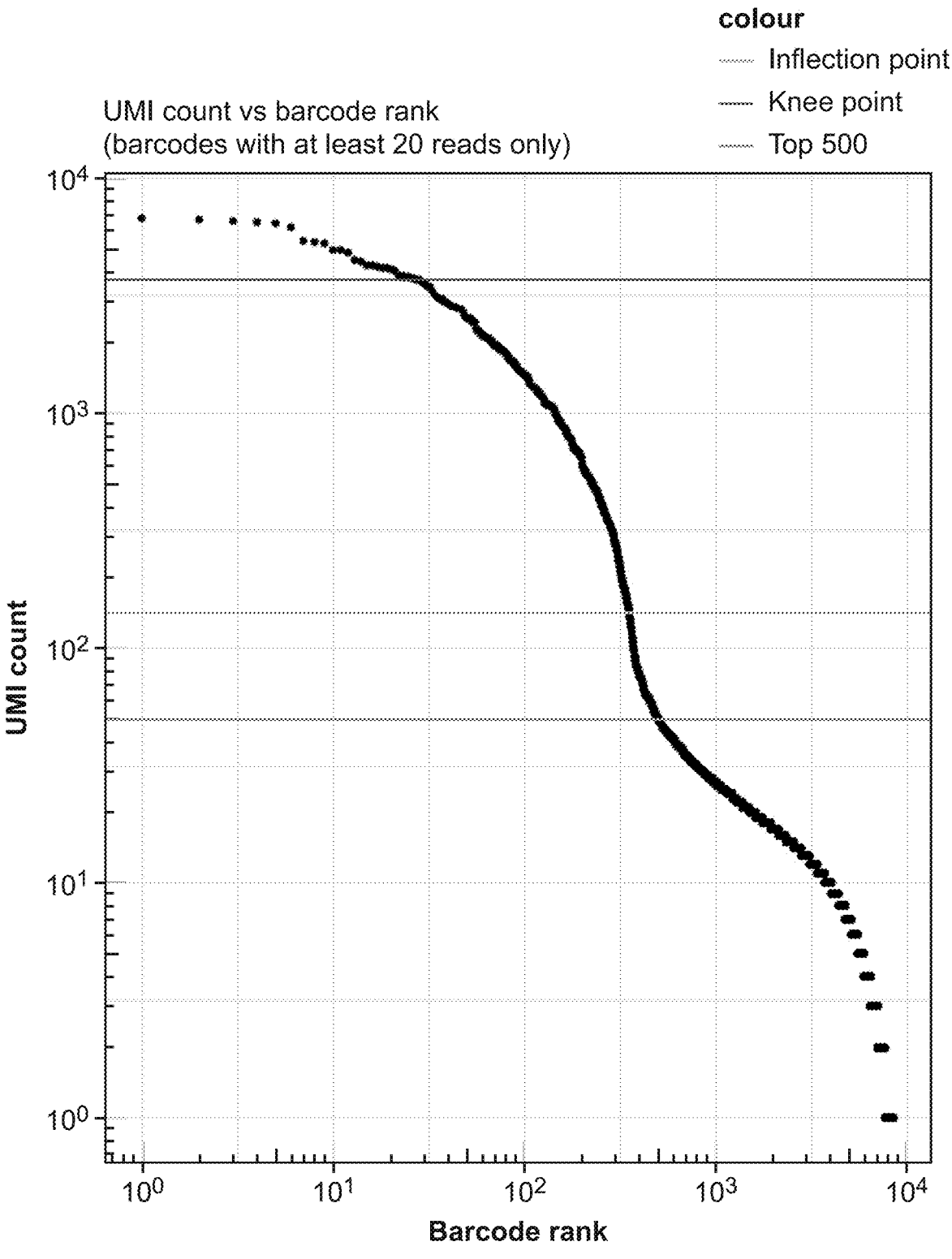
FIGS. 7A-7C show RNA quality of formalin-fixed and cleared samples, via SPLiT-seq analysis.
Figure 7B:
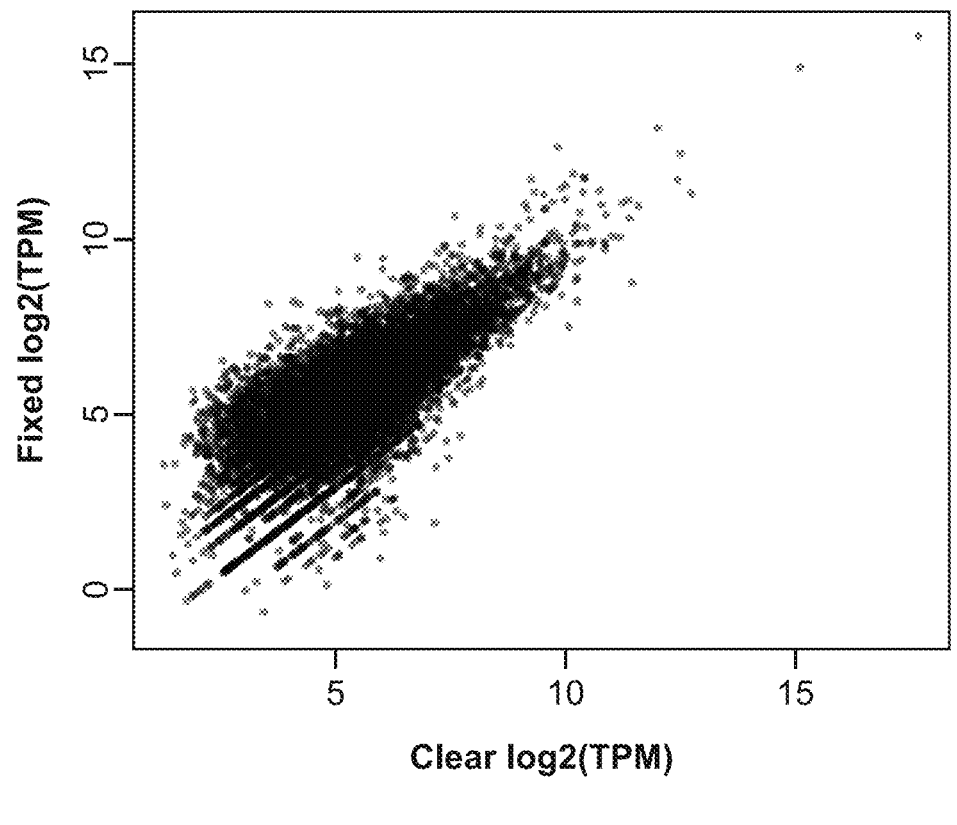
Figure 7C:
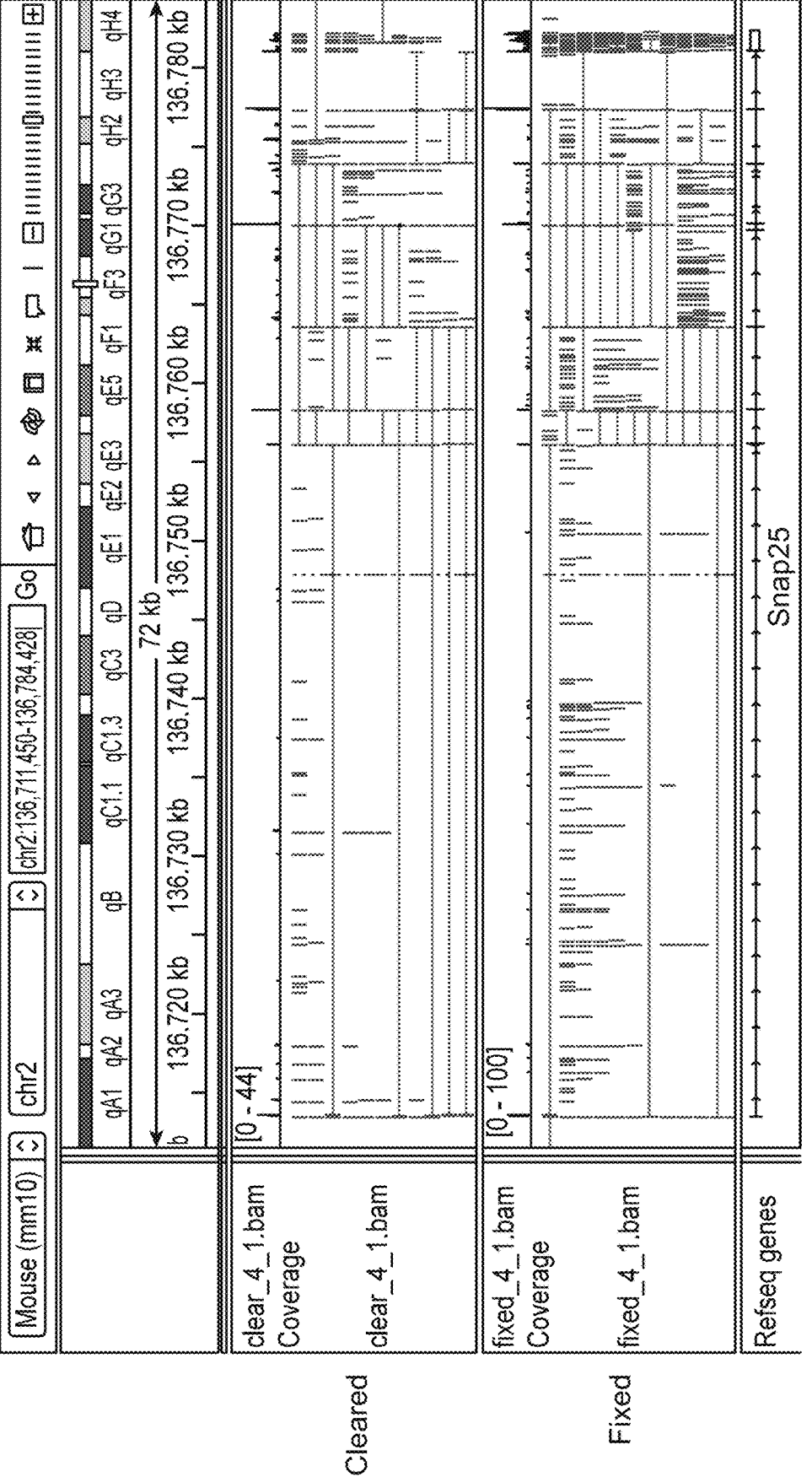

Cleared nuclei were isolated from Cy3-PA photolabeled mouse spinal cord, sorted for dye incorporation, the library prepared according to the SPLiT seq method and RNA sequenced using a MiSeq machine. Shown in FIG. 7A is the plotted count for unique barcodes versus the total barcode number that was detected. Two sub-libraries were then mixed (nuclei isolated from fixed, but not cleared tissue and nuclei isolated from fixed AND cleared tissue) in a 2:1 ratio (fixed:cleared). As shown in FIG. 7B, TPM count was plotted for both libraries and shows linear correlation, indicated that the process of clearing is not altering the sequencing result. Shown in FIG. 7C is a random region from the mouse chromosome 2 with reads generated from fixed, but not cleared, as well as fixed and cleared mouse spinal cord.

Example 6

3D analysis of DNA/RNA/Protein Composition in Mouse Lung

An adequately prepared piece of mouse lung is subjected to the clearing protocol, imaged, and a photoactivatable compound added to it in situ (the tissue was not moved).

Meanwhile, the area of interest is identified using the previously generated data, programmed for photoactivation, and photoactivated. The tissue is then unmounted, washed and rehydrated. The tissue then can be processed by either extracting the nuclei using a Dounce homogenizer, targeted isolation of the nuclei that then are stained with the relevant compound (e.g., streptavidin when photobiotin is used as the photoactivatable compound). Cleared nuclei are isolated from photolabeled lung, stained using a streptavidin-conjugated dye, and sorted for dye incorporation. The library is prepared according to the SPLiT seq method and RNA is sequenced using an adequate method. Alternatively, RNA can be analyzed by any method, including RT-PCR, electrophoresis, and the like.

For DNA sequencing, the process is similar; following isolation of nuclei and sorting, DNA can be sequenced using appropriate methods. DNA can also be analyzed, for example, by PCR, electrophoresis, or any other appropriate method.

For the protein analysis, mass-spectrographic readout (e.g., liquid chromatography/mass spec) or other suitable protein analytical methods can be used to determine the composition of proteins with incorporated PA-compound. Other protein analytical methods may include electrophoresis, protein blots, Edman degradation or other protein sequencing, and the like.

Example 7

3D analysis of DNA/RNA/Protein Composition in Spinal Cord

Figure 8A:
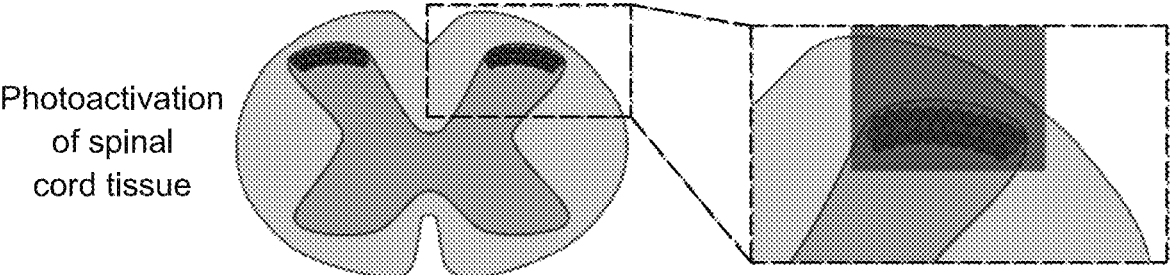
FIGS. 8A-8C show the use of 2-photon labeling of spinal cord tissue.

FIG. 8A is a drawing of a cross section of a mouse spinal cord, illustrating different areas of the spinal cord with dorsal layers indicated as colored circles. In the magnified panel, an area is highlighted that was subjected to photoactivation. Note that in this example the area of PA was not further refined—this is possible though since the resolution correlates with optical resolution of the lenses used. For example: A 20× lens will provide a 0.89 μm X 0.89 μm×1.6 μml resolution.

Figure 8B:
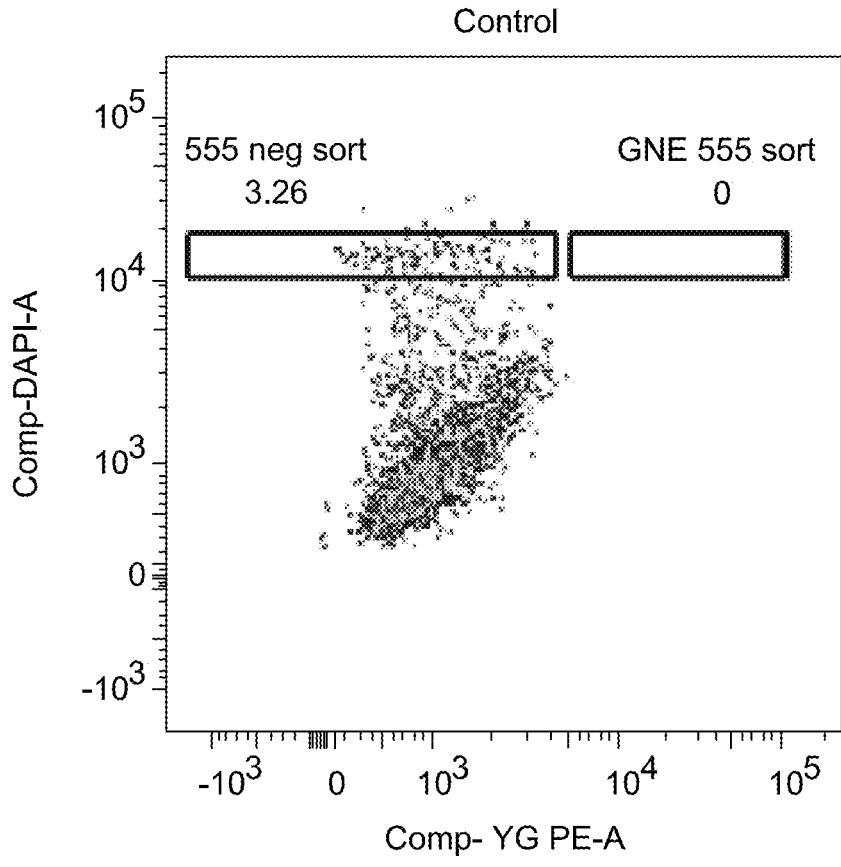

FIG. 8B shows a FACS plot of cleared, but not photoactivated nuclei isolated from a mouse spinal cord using the procedure described herein. The Y axis shows the signal for DAPI, a nuclear counterstain, while the X axis shows the PA dye (Cy3-PA). The boxes indicate single nuclei negative for incorporated Cy3 (left) or positive for incorporated Cy3 (right).

Figure 8C:
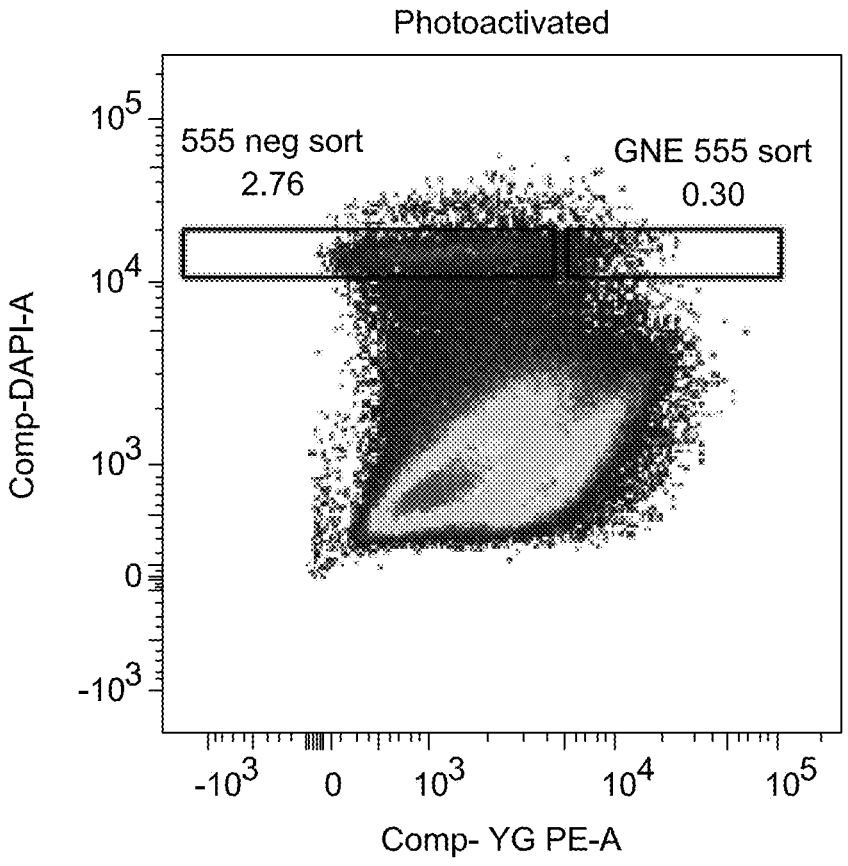
Figure 9B:
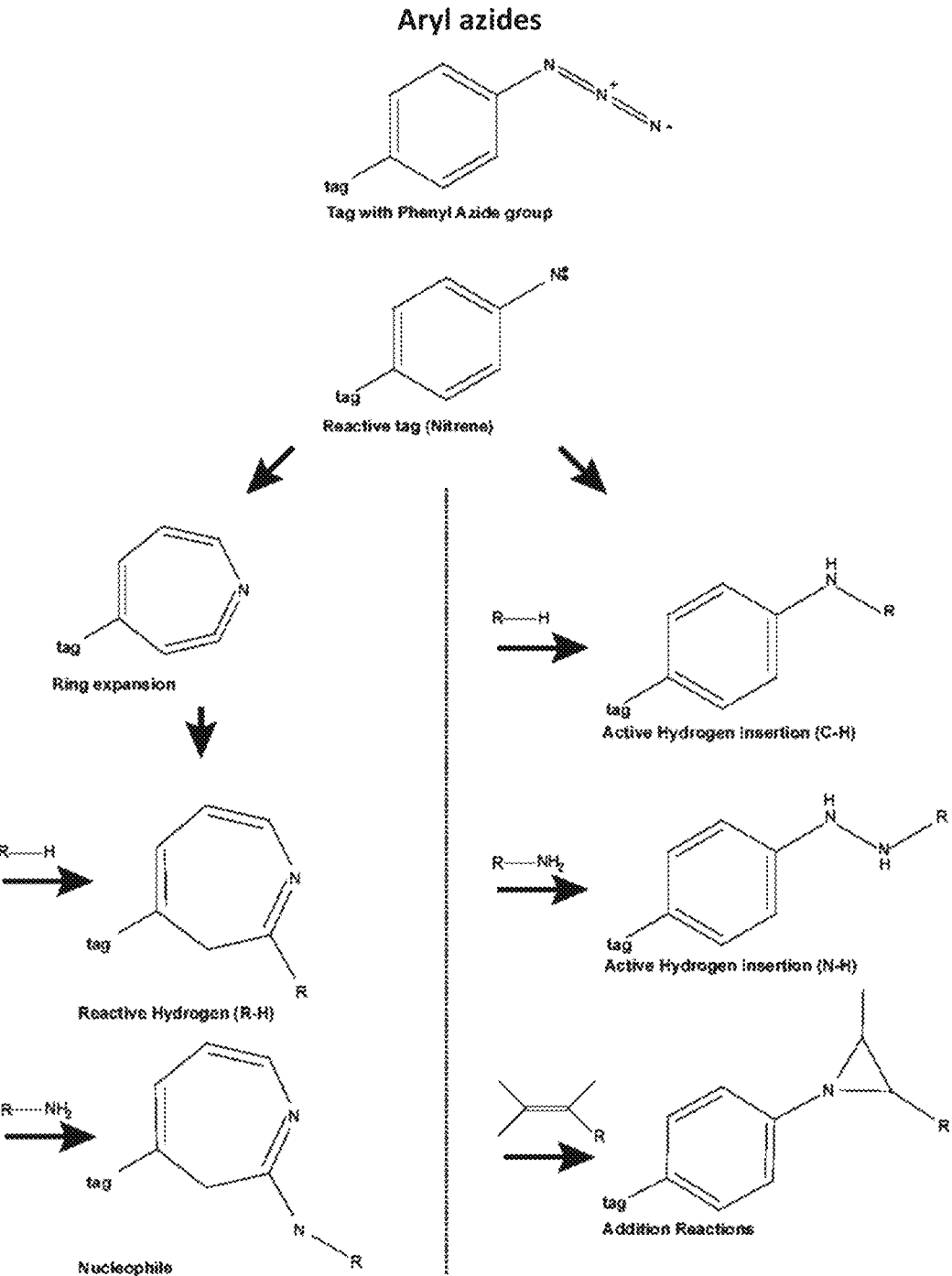
Figure 9C:
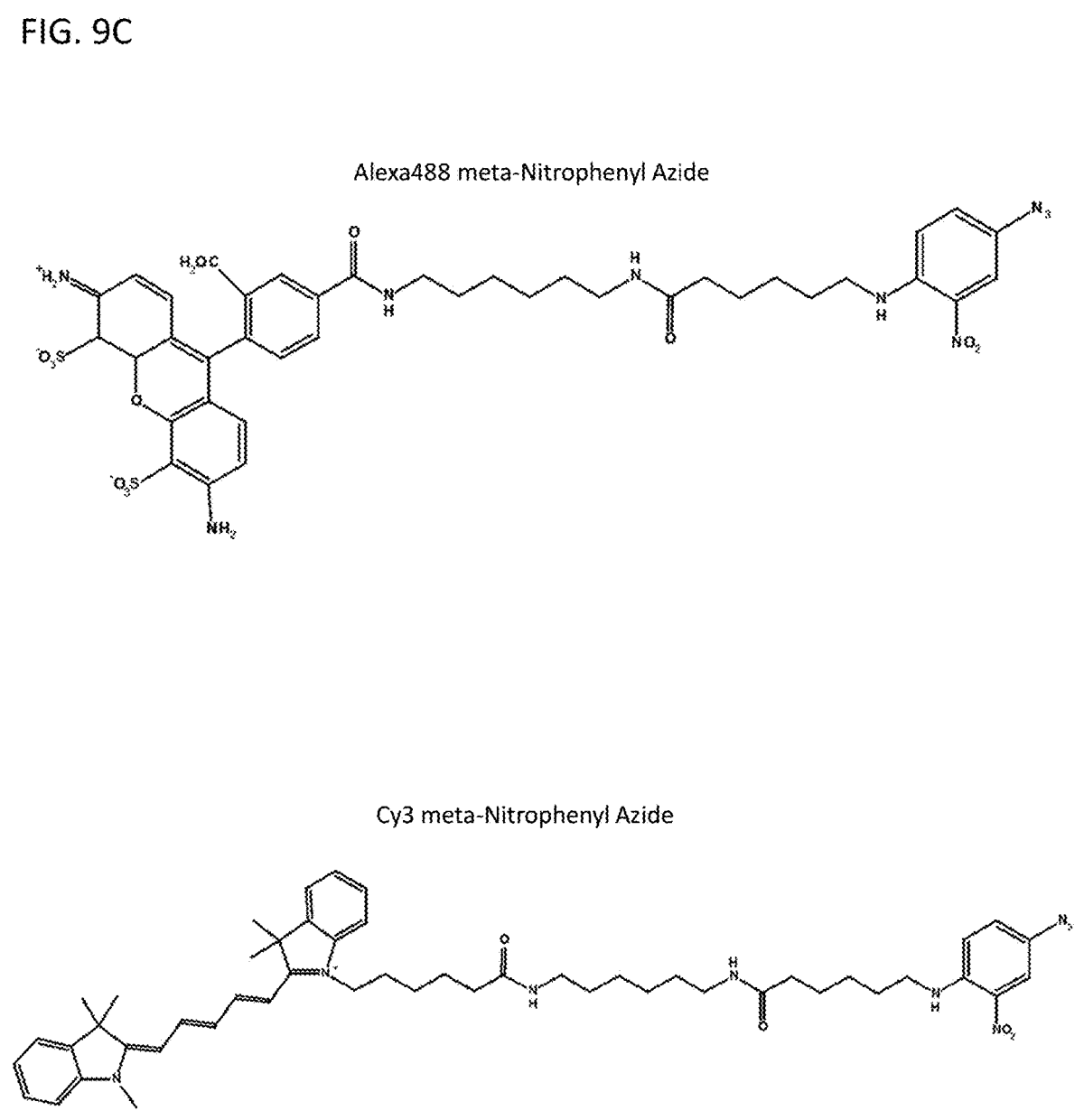
Figure 9C:
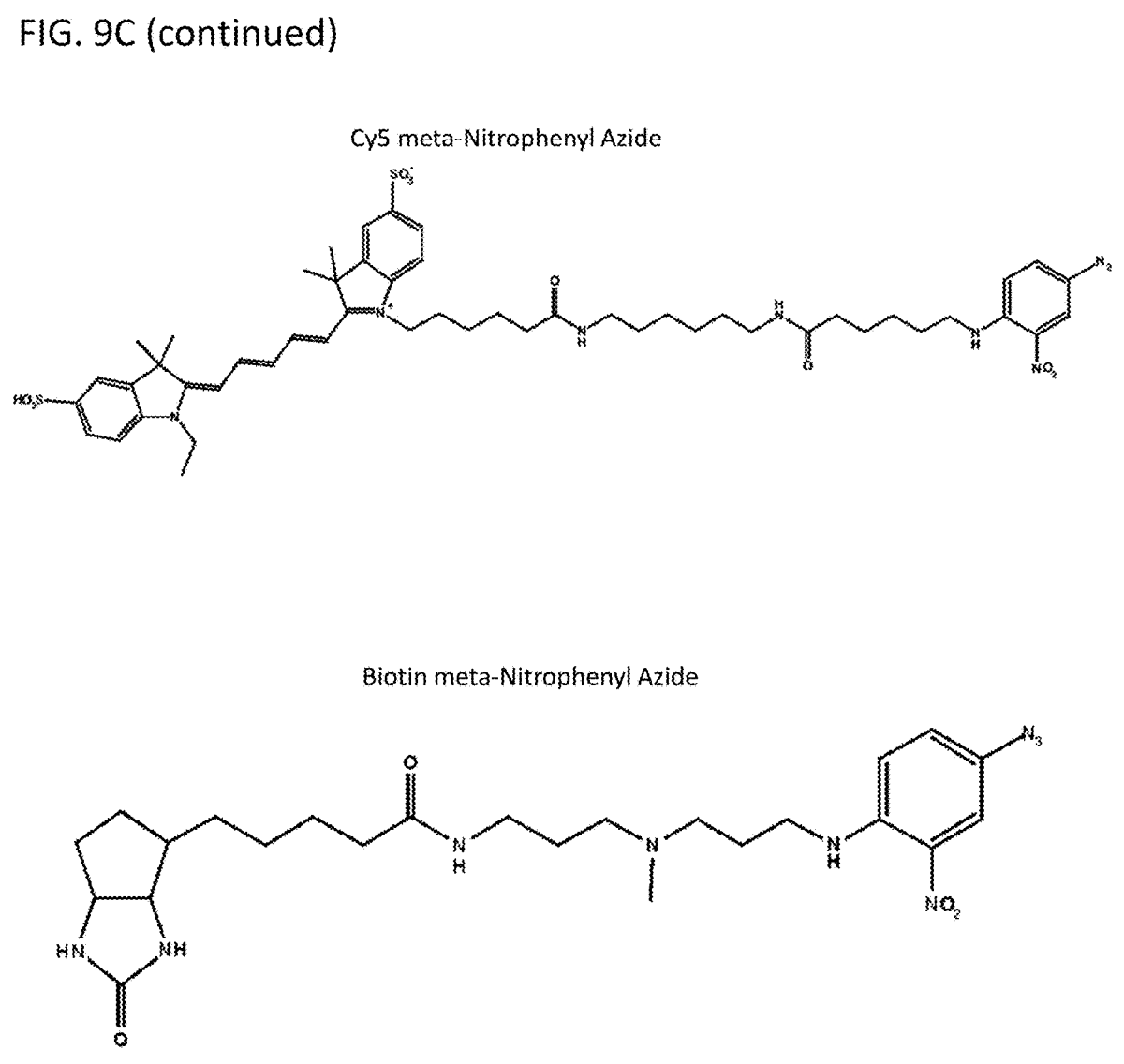

FIG. 8C shows a FACS plot of cleared and photoactivated nuclei isolated from a mouse spinal cord (indicated in FIG. 9A). The Y axis show the signal for DAPI, a nuclear counterstain, while the X axis shows the PA dye (Cy3-PA). The boxes indicate single nuclei negative for incorporated Cy3 (left) or positive for incorporated Cy3 (right).

Example 8

SPLiTseq of Cleared Nuclei From Spinal Cord

Figure 10A:
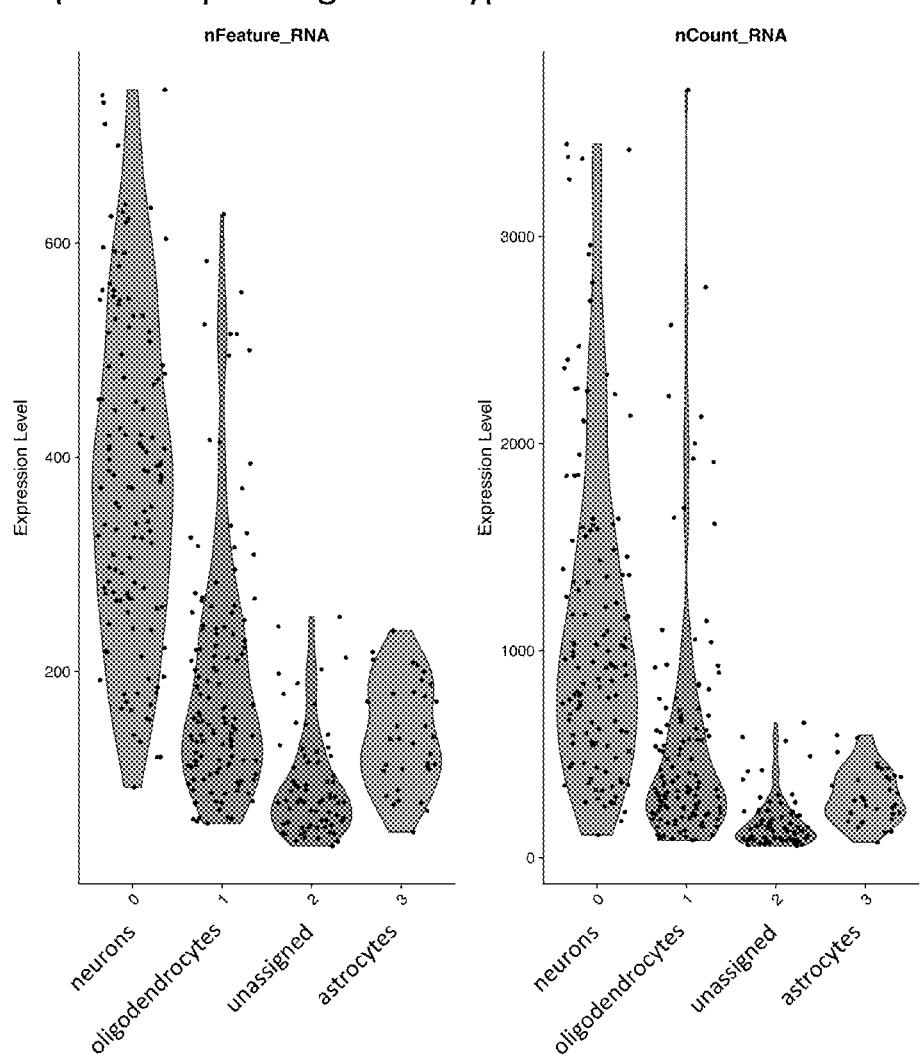
FIGS. 10A-10B show expression profiling of cleared nuclei from spinal cord, using SPLiT-seq analysis.
Figure 10B:
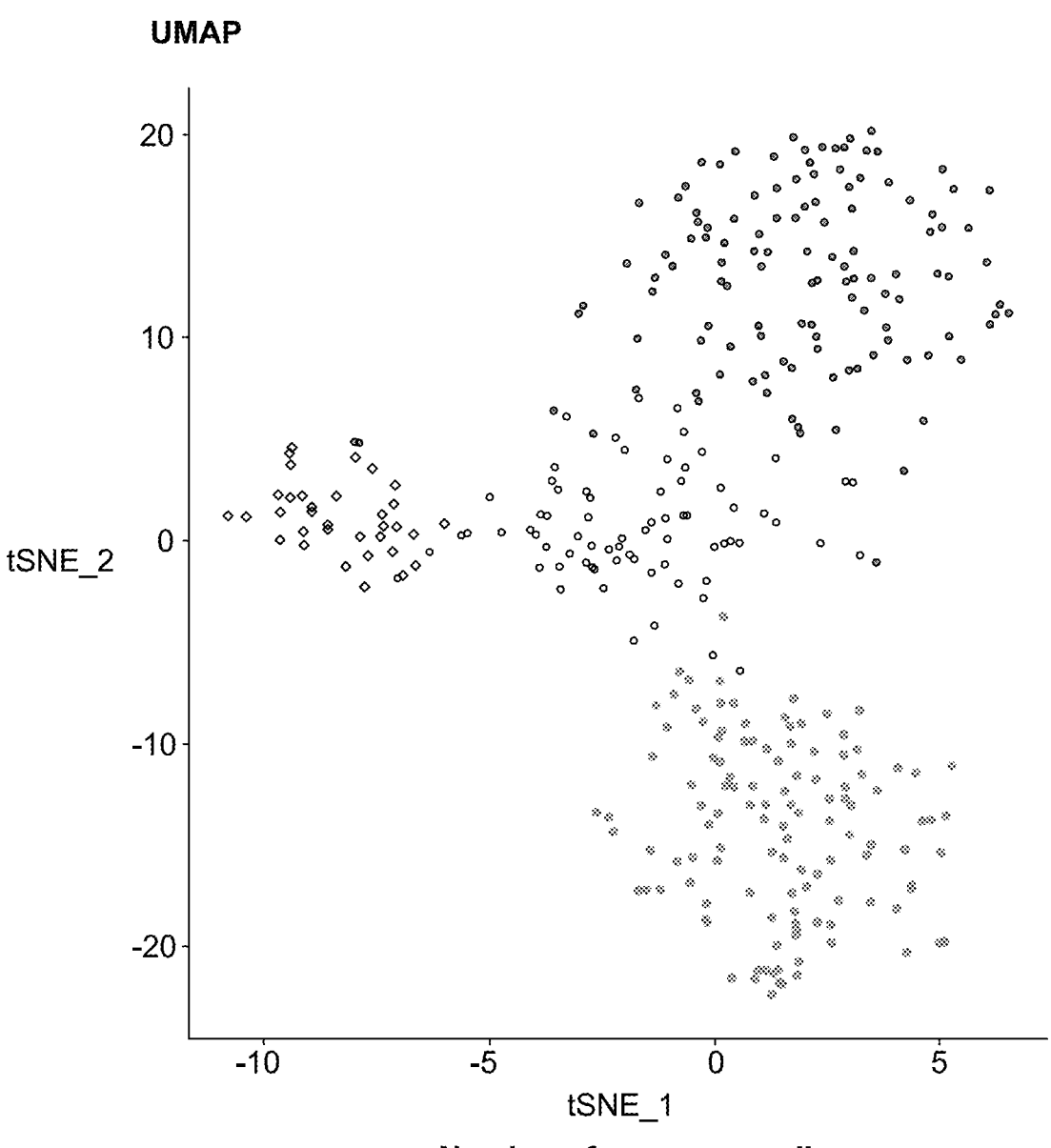

To show that cleared tissue can be analyzed by SPLiT-seq, mouse spinal cord was subjected to clearing as described in Example 1. Nuclei were isolated from the cleared tissue, and subjected to SPLiT-seq analysis. As shown in FIGS. 10A and 10B, SPLiT-seq expression profiling showed expression of markers of expected cells types present in the cleared tissue, including neurons, oligodendrocytes, and astrocytes. RNA expression profiles were determined based on an RNA expression database. FIG. 10A shows an nFeature plot (left) and an nCount plot (right) of the RNA expression levels. FIG. 10B shows a UMAP plot of the RNA expression levels.

REFERENCES

1. Olson, E., Levene, M. and Torres, R. (2016). Multiphoton microscopy with clearing for three dimensional histology of kidney biopsies. *Biomedical Optics Express*, 7(8), p.3089.

2. Rodrigues, S., Stickels, R., Goeva, A., Martin, C., Murray, E., Vanderburg, C., Welch, J., Chen, L., Chen, F. and Macosko, E. (2019). Slide-seq: A scalable technology for measuring genome-wide expression at high spatial resolution. *Science*, 363(6434), pp.1463-1467.

3. Schwarz, M. K., Scherbarth, A., Sprengel, R., Engelhardt, J., Theer, P., & Giese, G. (2015). Fluorescent-protein stabilization and high-resolution imaging of cleared, intact mouse brains. *PLoS ONE*, 10, 1-26.

4. Wang, X., Allen, W., Wright, M., Sylwestrak, E., Samusik, N., Vesuna, S., Evans, K., Liu, C., Ramakrishnan, C., Liu, J., Nolan, G., Bava, F. and Deisseroth, K. (2018). Three-dimensional intact-tissue sequencing of single-cell transcriptional states. Science, 361(6400), p.eaat5691.

What is claimed is:

1. A method for 3-dimensional expression profiling of an intact tissue or tissue sample, comprising:
  (a) providing a three-dimensional intact tissue or tissue sample;
  (b) clearing the sample;
  (c) contacting the tissue or tissue sample with a photo-activatable label;
  (d) subjecting a region of the tissue or tissue sample to a multi-photon laser, thereby labeling the region;
  (e) imaging the labeled region to create an image;
  (f) isolating the labeled region from the tissue or tissue sample;
  (g) determining a DNA, RNA, and/or protein composition of the isolated labeled region; and
  (h) combining the image with the DNA, RNA, and/or protein composition of the isolated labeled region to create a 3-dimensional expression profile of the intact tissue or tissue sample.

2. The method of claim 1, wherein the region is a cell, a subcellular compartment, an aggregate, or a secreted aggregate.

3. The method of claim 2, wherein the subcellular compartment is a nucleus.

4. The method of claim 1, wherein
the RNA composition is determined by sequencing, single cell RNA sequencing (scRNAseq), or SPLITseq, the protein composition is determined by mass spectrometry, and/or the DNA composition is determined by DNA sequencing.

5. The method of claim 1, wherein the photo-activatable label comprises one or more of:
(a) a detectable moiety;
(b) a light emitting moiety;
(c) fluorescent moiety;
(d) a chemiluminescent moiety:
(e) a bioluminescent moiety;
(f) an electrochemiluminescent moiety;
(g) a fluorophore;
(h) an antibody or a functional derivative thereof;
(i) a tag;
(i) an affinity tag;
(k) an epitope tag;
(1) a fluorescent tag;
(m) an oligonucleotide tag; and
(n) a biotin tag.

6. The method of claim 1, wherein the sample clearing process comprises dehydrating the sample and transferring the sample into a medium with a refraction index:

(a) similar to the tissue;
(b) matching the tissue; or
(c) between about 1.3 and about 1.6.

7. The method of claim 6, wherein the medium comprises a solution of Benzyl Alcohol, Benzyl Benzoate (BABB) or derivative thereof, with or without one or more of triethylamine, diphenyl ether, dibenzyl ether, α-tocopherol, and/or N,N,N',N'-Tetrakis (2-hydroxypropyl) ethylenediamine Quadrol.

8. The method of claim 7, wherein the medium comprises a BABB solution.

9. The method of claim 1, wherein the photo-activatable label is hydrophobic.

10. The method of claim 1, wherein the photo-activatable label comprises a phenyl azide group, an ortho-hydroxyphenyl azide group, a meta-hydroxyphenyl azide group, a tertrafluorophenyl azide group, an ortho-nitrophenyl azide group, a meta-nitrophenyl azide group, a diazirine group, an azido-methylcoumarin group, or a psoralen group.

11. The method of claim 1, wherein the multi-photon laser is a two-photon laser or a three-photon laser.

12. The method of claim 1, wherein the tissue or tissue sample is a fixed tissue or fixed tissue sample.

13. The method of claim 1, wherein the sample is dehydrated by a tert-butanol solution or a tert-butanol solution comprising trimethylamine, tetrahydrofuran, ethanol, or methanol.

14. The method of claim 1, wherein the labeled region is isolated by FACS sorting for the label.

15. The method of claim 1, wherein the isolated labeled region is a single nucleus or a single cell.

* * * * *